US012778409B2

(12) United States Patent
Vaghefi Rezaei et al.

(10) Patent No.: US 12,778,409 B2
(45) **Date of Patent: *Nov. 3, 2026**

(54) SYSTEMS AND METHODS FOR PROCESSING OF FUNDUS IMAGES

(71) Applicant: TOKU EYES LIMITED, Newmarket (NZ)

(72) Inventors: Seyed Ehsan Vaghefi Rezaei, San Diego, CA (US); David Michael Squirrell, Westlake (NZ); Song Yang, Grafton (NZ); Songyang An, Newmarket (NZ); Li Xie, Grey Lynn (NZ)

(73) Assignee: Toku Eyes Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 19/368,947

(22) Filed: Oct. 24, 2025

(65) Prior Publication Data

US 2026/0047753 A1 Feb. 19, 2026

Related U.S. Application Data

(63) Continuation of application No. 19/017,193, filed on Jan. 10, 2025, now Pat. No. 12,471,770, which is a (Continued)

(30) Foreign Application Priority Data

May 24, 2023 (AU) ................................ 2023901630
Dec. 18, 2023 (AU) ................................ 2023904102

(51) Int. Cl.
*A61B 3/00* (2006.01)
*A61B 3/12* (2006.01)
(Continued)

(52) U.S. Cl.
CPC .............. *A61B 3/0025* (2013.01); *A61B 3/12* (2013.01); *A61B 5/02007* (2013.01); (Continued)

(58) Field of Classification Search
CPC ..... A61B 3/0025; A61B 3/12; A61B 5/02007; A61B 5/486; A61B 5/7267; A61B 5/7275
See application file for complete search history.

(56) References Cited

U.S. PATENT DOCUMENTS

2020/0375521 A1 12/2020 Hadoux et al.
2021/0388442 A1 12/2021 Schiederig et al.
(Continued)

FOREIGN PATENT DOCUMENTS

CN 111712186 B * 6/2024 ............. G06V 40/18
JP 2022544169 A * 10/2022 ......... A61K 38/2006
(Continued)

*Primary Examiner* — Khai M Nguyen
(74) *Attorney, Agent, or Firm* — Knobbe, Martens, Olson & Bear, LLP

(57) ABSTRACT

Systems and methods for determining one or more recommendations for management of wellbeing of an individual are disclosed. An indication of relative cardiovascular aging of the individual is determined based at least in part on determining an indication of relative cardiovascular aging of the first individual, based at least in part on a predicted risk of cardiovascular disease (CVD) of the individual determined by a deep learning model based on one or more fundus images; and determining the at least one recommendation for management of the individual's wellbeing based at least in part on the determined indication of relative cardiovascular aging of the first individual.

15 Claims, 14 Drawing Sheets

Related U.S. Application Data continuation of application No. 18/674,111, filed on May 24, 2024, now Pat. No. 12,193,739.

(51) Int. Cl.
*A61B 5/00* (2006.01)
*A61B 5/02* (2006.01)

(52) U.S. Cl.
CPC ............ *A61B 5/486* (2013.01); *A61B 5/7267* (2013.01); *A61B 5/7275* (2013.01)

(56) References Cited

U.S. PATENT DOCUMENTS

| | | | | |
|---|---|---|---|---|
| 2022/0175325 | A1 | 6/2022 | Fukushima et al. | |
| 2022/0301709 | A1 | 9/2022 | Choi et al. | |
| 2022/0378378 | A1 | 12/2022 | Cho et al. | |
| 2023/0047199 | A1 | 2/2023 | Oh et al. | |
| 2024/0186016 | A1* | 6/2024 | Kesar | G16H 50/70 |
| 2024/0389850 | A1* | 11/2024 | Vaghefi Rezaei | A61B 5/486 |
| 2025/0025045 | A1* | 1/2025 | Tran | A61B 3/16 |
| 2025/0143562 | A1* | 5/2025 | Vaghefi Rezaei | A61B 5/7275 |
| 2025/0308701 | A1* | 10/2025 | Vaghefi Rezaei | G16H 30/40 |

FOREIGN PATENT DOCUMENTS

| | | | | | |
|---|---|---|---|---|---|
| KR | 20210069944 | A | * | 6/2021 | G01J 3/4406 |
| WO | WO-2022261513 | A1 | * | 12/2022 | A61B 3/12 |

* cited by examiner

SYSTEMS AND METHODS FOR PROCESSING OF FUNDUS IMAGES

CROSS-REFERENCE TO RELATED APPLICATION

This application is a continuation application of U.S. application Ser. No. 19/017,193, filed Jan. 10, 2025, which is a continuation application of U.S. application Ser. No. 18/674,111, filed May 24, 2024, which is based on Australian patent application no. 2023901630, filed May 24, 2023, and Australian patent application no. 2023904102, filed Dec. 18, 2023, the entire contents of which are incorporated herein by reference.

TECHNICAL FIELD

The present technology relates to systems and methods for processing fundus images, more particularly the processing of fundus images to determine a risk level of cardiovascular disease (CVD), and determination of an indicator of relative cardiovascular aging.

BACKGROUND

Cardiovascular disease (CVD) is the leading cause of hospitalisation and premature death in the USA, and its most common comorbidities include non-modifiable factors such as age and gender, and modifiable factors such as glycaemic control, blood pressure, cholesterol, and exposure to smoking.

National CVD risk management guidelines recommend that treatment decisions should be informed by their predicted CVD risk. CVD risk varies greatly across a population (from minimal to severe), and identification of personal CVD risk using current statistical methods has issues with accuracy. The modest accuracy of current CVD risk prediction equations (i.e., resulting in too many false positives and false negatives) is largely because the available predictors are all indirect measures of CVD. These equations use regression models applying parameters such as age, sex, ethnicity, socioeconomic deprivation, smoking, diabetes duration, systolic blood pressure, total cholesterol-to-HDL ratio, glycated haemoglobin A1c (HbA1c), and urine albumin-to-creatinine ratio (ACR). More accurate CVD risk stratification is needed to better target medications and treatment program to appropriate recipients.

The retina is the only part of the human vasculature that is directly visible by non-invasive means. Several studies have recently shown that an artificial intelligence (AI) deep learning retinal image algorithm can be used for estimating CVD risk. However, in all of these methods, the retinal images are trained against a single label. Some studies have used the chronological age as the "label" for training, and the outcome of the model is called "retinal age". Any discrepancies between the label (chronological) and estimated (retinal) ages is considered as an indication of higher risk of CVD event. Other studies have used the CVD risk calculated by conventional equations as the "label". In this approach, the outcome is a single number (presumably perceived risk), which has proven to be inaccurate. Furthermore, neither of these approaches identify the major contributors of the CVD risk (e.g. blood pressure vs cholesterol vs glycaemic control vs other contributors).

It is an object of the present disclosure to address at least one of the foregoing problems or at least to provide the public with a useful choice.

Further aspects and advantages of the present disclosure will become apparent from the ensuing description which is given by way of example only.

SUMMARY

The present technology provides systems and methods for retinal image analysis using artificial intelligence (AI). Because retinal images, also referred to as fundus images, are routinely taken as part of medical screening procedures (for example, retinal screening for diabetic retinopathy), these images have the potential to be rapidly analysed at low cost for improving CVD risk prediction, and made available immediately to the patient and their health care provider with no additional burden to the patient.

According to one aspect of the present technology there is provided a method of determining an indication of relative cardiovascular aging of an individual, comprising: determining a degree of similarity between a predicted risk of cardiovascular disease (CVD) of a first individual and the risk of CVD for a set of individuals belonging to a chronological age group to which the first individual also belongs, wherein the predicted risk of CVD is determined by a deep learning model based on one or more fundus images; determining an average chronological age of individuals closest to the first individual in terms of predicted risk of CVD; determining a mean expected chronological age for a person with the predicted risk of CVD of the first individual; and determining the indication of relative cardiovascular aging of the first individual based on the determined degree of similarity, the determined average chronological age, and the determined mean expected chronological age.

In examples, determining the indication of relative cardiovascular aging ("Cardiac BioAge") of the first individual comprises the calculation:

$$\text{Cardiac } BioAge_x = P(\text{risk}(x)|x \in X) * \underline{\text{age}(X)} + (1 - P(\text{risk}(x)|x \in X)) * \underline{\text{age}(Y|x \sim Y)}$$

where x refers to the first individual, and X is the set of individuals who are in the same age group as the first individual; where P(risk(x)|x∈X) is the conditional probability that first individual x has CVD risk, risk(x), given that that the first individual belongs the set X of individuals who have similar age; where $\underline{\text{age(X)}}$ is the mean age for set X; and where $\underline{\text{age(Y|x\sim Y)}}$ is the mean age of patient points who are close to the first individual x.

In examples the set of individuals may comprise individuals of the same gender as the first individual.

In examples implementation of $\underline{\text{age(Y|x\sim Y)}}$ may comprise the components $$\text{similarity magnitude} * \text{cosine similarity age} + (1 - \text{similarity magnitude}) * \text{risk extrapolated age.}$$

According to one aspect of the present technology there is provided a method for determining a recommendation for management of wellbeing of an individual, comprising: determining an indication of relative cardiovascular aging ("Cardiac BioAge") of the individual, based at least in part on a predicted risk of cardiovascular disease (CVD) of the individual determined by a deep learning model based on one or more fundus images; and determining the recommendation for management of the individual's wellbeing based at least in part on the determined Cardiac BioAge.

According to one aspect of the present technology there is provided a method for determining a recommendation for management of wellbeing of an individual, comprising: determining an indication of relative cardiovascular aging ("Cardiac BioAge") of the individual, based at least in part on a predicted risk of cardiovascular disease (CVD) of the individual determined by a deep learning model based on one or more fundus images; determining a difference ("AgeGap") between an actual chronological age of the individual and the Cardiac BioAge determined for the individual; and determining the recommendation for management of the individual's wellbeing based at least in part on the determined AgeGap.

According to one aspect of the present technology there is provided a method, comprising: determining an indication of relative cardiovascular aging of an individual, based at least in part on a predicted risk of cardiovascular disease (CVD) of the individual determined by a deep learning model based on one or more fundus images; determining the relative contribution of one or more risk contributing factors to the indication of relative cardiovascular aging.

In examples the risk contributing factors may include two or more of: blood pressure, glycated haemoglobin A1c (HbA1c), total cholesterol, and glycaemic control.

In examples the method may comprise determining a difference ("AgeGap") between the actual chronological age of the individual and the indication of relative cardiovascular aging determined for the individual.

In examples the method may comprise comparing the AgeGap of the individual with the AgeGaps of a set of individuals belonging to a chronological age group to which the individual belongs. In examples the method may comprise determining a relative position of the individual within the set of individuals based on AgeGap. In examples the method may comprise determining one or recommendations for management of the individual's wellbeing based at least in part on the relative position of the individual within the set of individuals based on AgeGap.

In examples a relative contribution of one or more of the risk contributing factors may be determined based on the relative position of the individual within the set of individuals based on AgeGap.

In examples, the relative contribution of the one of more of the risk contributing factors may be used to determine one or recommendations for management of the individual's wellbeing. For example, the one or more recommendations may include initiating testing and/or investigation for conditions associated with the one or more risk contributing factors.

According to one aspect of the present technology there is provided a method of predicting a risk of cardiovascular disease (CVD) from one or more fundus images, the method performed by one or more processors. In examples the method comprises processing one or more fundus images associated with an individual using a Quality Assurance (QA) set of one or more convolutional neural networks (CNNs) to determine whether the one or more fundus images are of sufficient quality for further processing. In examples the method further comprises processing the one or more fundus images determined to be of sufficient quality for further processing using an eye-identification set of one or more CNNs (eye-ID CNN), to identify the one or more fundus images belonging to a single eye. In examples the method further comprises processing the one or more fundus images using a plurality of risk contributing factor sets of one or more CNNs (RCF CNN), wherein each RCF CNN is configured to output an indicator of probability of the presence of a different risk contributing factor in each of the one or more fundus images, wherein at least one of the RCF CNNs is configured in a jury system model comprising a plurality of jury member CNNs, wherein each jury member CNN is configured to output a probability of a different feature in the one or more fundus images, and the outputs of the plurality of jury member CNNs are processed to determine the indicator of probability of the presence of the risk contributing factor output by the RCF CNN. In examples the method further comprises producing an individual feature vector based on meta-information for the individual, and the outputs of the plurality of RCF sets of one or more CNNs. In examples the method further comprises processing the individual feature vector using a CVD risk prediction neural network model to output a prediction of overall CVD risk for the individual, wherein the CVD risk prediction neural network model is configured to determine a relative contribution of each of the risk contributing factors to the prediction of overall CVD risk. In examples the method further comprises reporting the overall CVD risk, comprising reporting the relative contribution of each of the risk contributing factors to the overall CVD risk.

According to one aspect of the present technology there is provided a method of predicting cardiovascular disease (CVD) from one or more fundus images, the method performed by one or more processors, the method comprising: processing one or more fundus images associated with an individual using a plurality of sets of one or more convolutional neural networks (CNNs). In examples the plurality of sets of one or more CNNs may include two or more of: a Quality Assurance (QA) set of one or more CNNs, an eye-identification (eye-ID) set of one or more CNNs, a localized change set of one or more CNNs, a global change set of one or more CNNs, and a metarepresentation set of one or more CNNs.

According to one aspect of the present technology there is provided a method of predicting cardiovascular disease (CVD) from one or more fundus images, the method performed by one or more processors, the method comprising: processing one or more fundus images associated with an individual using a plurality of risk contributing factor (RCF) sets of one or more CNNs, wherein each RCF set of one or more CNNs is configured to output an indicator of probability of the presence of a different risk contributing factor in each of the one or more fundus images. In examples the method comprises producing an individual feature vector based on meta-information for the individual, and the outputs of the plurality of RCF sets of one or more CNNs. In examples the method comprises processing the individual feature vector using a CVD risk prediction neural network model to output a prediction of CVD risk for the individual.

In examples, one or more fundus images may be processed in order to predict a risk of cardiovascular disease (CVD) from the one or more fundus images. In examples the method may comprise processing one or more fundus images associated with an individual using a Quality Assurance (QA) set of one or more CNNs to determine whether the one or more fundus images are of sufficient quality for further processing. In examples the method may comprise processing the one or more fundus images determined to be of sufficient quality for further processing using an eye-identification (eye-ID) set of one or more CNNs, to identify the one or more fundus images belonging to a single eye. In examples the method may comprise processing the one or more fundus images using a plurality of risk contributing factor (RCF) sets of one or more CNNs, wherein each RCF set of one or more CNNs is configured to output an indicator of probability of the presence of a different risk contributing factor in each of the one or more fundus images. In examples the method may comprise producing an individual feature vector based on meta-information for the individual, and the outputs of the plurality of RCF sets of one or more CNNs. In examples the method may comprise processing the individual feature vector using a CVD risk prediction neural network model to output a prediction of CVD risk for the individual.

In examples, the one or more fundus images may be processed using a Quality Assurance (QA) set of one or more convolutional neural networks to determine whether the one or more fundus images are of sufficient quality for further processing.

In examples, classifying an image as unsuitable may comprise determining that the image is not directed to a relevant region of an eye of the individual. In examples, determining the image is unsuitable may comprise determining that at least one property of the image is unsuitable. For example, the image may be determined as being oversaturated, underexposed, out of focus, or blurred.

In examples, a notification may be issued warning a user that the one or more fundus images supplied are unsuitable. This enables one or more replacement images to be supplied.

In examples the one or more fundus images may be adjusted prior to processing. In examples, the image adjustment may be normalisation of the images, for example spatial or intensity normalisation. In examples, spatial normalisation may include one or more of: cropping, scaling, and rotation of the one or more fundus images.

In examples, a color balancing process may be performed on the one or more fundus images. In an example, a Gaussian filter may be applied to the one or more fundus images in order to perform color balancing. Image quality, as it pertains to color, can vary significantly between different fundus camera technologies and/or models. Colour balancing reduces the mismatch in images resulting from this, to assist with further processing. In examples, the one or more fundus images may be converted from a colour image into a greyscale or mohba1nochrome image.

In examples, a brightness adjustment process may be performed on the one or more fundus images. Image brightness can greatly vary due to environmental conditions (for example, lighting within a clinic) and patient pupil size. Brightness adjustment normalizes these variations to assist with further processing.

In examples in which the one or more fundus images comprises a plurality of fundus images, the plurality of fundus images may be processed using an eye-identification (eye-ID) set of one or more convolutional neural networks configured to group the fundus images as belonging to a single eye—for example, for future clinical results aggregation. In examples the eye-ID CNN operates by identifying an eye as left-eye or right-eye, understanding the “likeness” of several images, and one or more parameters including, but not limited to, image time stamp and patient unique ID. A grouping of images may be referred to as an image set.

In examples, one or more CNNs may be configured to identify a relative location of the one or more fundus images on the retina. For example, the one or more CNNs may be configured to determine whether the one or more fundus images are macula-centred or disk-centred. Two main landmarks of the retina are the macula, which has the densest photoreceptor concentration and is responsible for central vision, and the disk, where the optic nerve enters the eye. In examples, the eye-ID CNNs may be configured to determine if the one or more fundus images are foveal centred. In examples, the eye-ID CNNs may be configured to identify a relative location of the one or more fundus images on the retina.

In examples, one or more CNNs may be configured to determine a device, or characteristic of the device, used to capture the fundus image. In examples the one or more CNNs may be configured to determine whether the device utilises flash photography or white LED confocal photography. In examples, processing of the fundus image may be based at least in part on determination of the device, or the characteristic of the device. In examples, adjustment of the one or more fundus images prior to processing may be based at least in part on the determination of the device, or the characteristic of the device.

In examples, the one or more fundus images are processed by a plurality of risk contributing factor (RCF) sets of one or more CNNs, each RCF set of one or more CNNs configured to output an indication of the probability of the presence of a different risk contributing factor. In examples, the risk contributing factors may include two or more of: glycaemic control, blood pressure, cholesterol, and exposure to smoking. In examples, each of the CNNs may produce a probability of an indicator of this risk contributing factor. For example, the CNNs may look for “localized” signs of biological changes and physiological changes (e.g. microaneurysms, oedema, etc.) changes, and or “global” changes in an image that could indicate presence of glycaemic control, blood pressure, cholesterol, and exposure to smoking (e.g. pigmentary changes in the peripapillary region, arterial/venous crossing deformations, vascular tortuosity changes, vascular calibre changes, etc.). In examples the signs may include, but not be limited to: drusen appearance, clustering, and/or location; pigmentation change in density and/or location; arteriovenous crossing; change in arteriovenous crossing calibre and/or thickness change; arteriovenous tortuosity; retinal oedema size and/or pattern; and/or microaneurysms concentration.

In examples the plurality of risk contributing factor (RCF) sets of one or more CNNs may be configured to respectively target a plurality of labels selected from the group of: Retinopathy, Maculopathy, HbA1c, Systolic Blood Pressure, Drusen, Age-related macular degeneration (AMD), Smoking status, Total Cholesterol, and Macular Pigmentation Abnormalities.

In examples, at least one of the RCF CNNs may be configured in a jury system model comprising a plurality of jury member CNNs, wherein each jury member CNN is configured to output a probability of a different feature in the one or more fundus images, and the outputs of the plurality of jury member CNNs are processed to determine the indicator of probability of the presence of the risk contributing factor output by the RCF CNN.

For example, investigation of each risk contributing factor (e.g. glycaemic control, blood pressure, cholesterol, and exposure to smoking) may include a plurality (for example, at least five) of jury members. Each jury member may be configured to output a probability. The jury system model may produce a final probability based on the outcomes from each jury member. In examples the outputs of the plurality of jury member CNNs may be processed to determine the indicator of probability of the presence of the risk contributing factor output by the RCF CNN based on an expected population baseline for a population to which the individual belongs.

In examples, the outputs from the risk contributing factor (RCF) sets of one or more CNNs are aggregated using minimum, maximum, mean, and median in both model-level and image-level to generate an individual-level fundus image feature vector. In examples, the raw output of each model may be several floating values, where the length of output is model-dependent. The output aggregation firstly happens on a model-level. For example, for an input fundus image, five juror models give probabilities from 0 to 1, i.e. a minimum of 0 and a maximum of 1 (e.g. a decimal value such as 0.01454), and the probabilities for each grade level across five models are also aggregated. In examples, the output of the models are floating-point numbers and after the aggregation using a mathematical operation (including, but not limited to, weighted mean, min, max, etc.), the final output is still in the form of floating numbers. In examples, these floating-point numbers, are concatenated to form a one-dimensional array (i.e. the individual-level fundus image feature vector). In examples, meta-information of an individual associated with the one or more fundus images is combined with the individual-level fundus image feature vector to produce an individual feature vector. In examples a meta-information vector is produced from the meta-information. In examples, the meta-information is pre-processed using one or more of standardisation and one-shot encoding. For example, numerical feature such as age may be standardised to have a mean 0 and standard variance 1. For example, categorical features (e.g. gender and ethnicity) may be converted from string data to numerical vectors using one-shot encoding. In examples, the individual-level fundus image feature vector and the meta-information vector may be concatenated to produce the individual feature vector. This provides a metarepresentation understandable by neural networks.

In examples the CVD risk prediction neural network model utilises a fully connected neural network (FCNN). In examples the FCNN may have at least 5 layers. In examples, the relative contribution of each modifiable factor (e.g. glycaemic control, blood pressure, cholesterol, and exposure to smoking) to the overall CVD risk score is determined. This combination is not an equation, but rather an algorithmic approach, where the patient biometrics are combined and weighted appropriately with their retinal images, within the deeper layers of the overall FCNN design.

In examples, the functionality of two or more of the respective sets of one or more convolutional neural networks disclosed herein may be provided by a single set of one or more convolutional neural networks.

In examples, the system may be configured to report CVD risk on one or more of: an individual level, and a population level. At an individual level, an individual overall CVD risk may be reported—i.e. the overall risk of CVD to an individual associated with processed fundus images. In examples, the system may be configured to report on the contributing factors to the individual overall CVD risk, including non-modifiable contributing factors (e.g. based on patient meta-information such as age, gender, and/or ethnicity) and modifiable contributing factors (e.g. based on glycaemic control, blood pressure, cholesterol, and exposure to smoking). In examples the system may be configured to identify the relative contribution of the respective modifiable contributing factors. In examples the system may be configured to rank the modifiable contributing factors according to their relative contribution to the individual overall CVD risk.

At a population level, the system may be configured to report analysis is presented where the overall cohort cardiovascular risk profile and its contributing factors are generated. By way of example, the cohort may be that a population at local, regional, or national levels, the population of a healthcare provider, that of an organisation, or subsets thereof (for example, risk levels within the overall population). Similarly to the individual overall CVD risk, the system may be configured to report on the respective relative contributions of modifiable contributing factors at a population level.

In examples, the system may be configured to provide a recommendation for management of an individual's condition based on the determined risk. For example, a scale of risk levels may be provided, each risk level having an associated recommendation. In examples, at least one recommendation may be provided based on the relative contribution of each modifiable contributing factor. Such recommendations may relate to one or more of: lifestyle (e.g. diet and exercise), further clinical assessments (e.g. cardiologist consultation), or medication (e.g. adherence) decisions.

In examples, the results could be sent to an agency for further analysis, e.g. a healthcare payer for population health analysis.

In examples, the system may be configured to compare at least one of the overall CVD risk, and the relative contribution of each of the risk contributing factors to the overall CVD risk, of the individual to at least a portion of a population of individuals for whom the overall CVD risk is predicted by the CVD risk prediction neural network model, and report an indication of the comparison.

In examples, the system may be configured to predict a change to the overall CVD risk based on a change to one or more of the risk contributing factors. In examples the system may be configured to predict a group overall CVD risk for at least a portion of a population of individuals for whom the overall CVD risk is predicted by the CVD risk prediction neural network model. In examples, the system may be configured to predict a change to the group overall CVD risk based on a change to one or more of the risk contributing factors for at least a portion of the population of individuals.

According to one aspect of the present technology there is provided a system comprising a memory storing program instructions; and at least one processor configured to execute program instructions stored in the memory, wherein the program instructions cause the processor to perform the method of determining an indication of relative cardiovascular aging of an individual described herein.

According to one aspect of the present technology there is provided a computer program product, the computer program product comprising: a non-transitory computer-readable medium having computer-readable program code stored thereon, the computer-readable program code comprising instructions that when executed by a processor, cause the processor to perform the method of determining an indication of relative cardiovascular aging of an individual described herein.

According to one aspect of the present technology there is provided a system comprising a memory storing program instructions; and at least one processor configured to execute program instructions stored in the memory, wherein the program instructions cause the processor to perform the determining an indication of relative cardiovascular aging of an individual described herein.

According to one aspect of the present technology there is provided a computer program product, the computer program product comprising: a non-transitory computer-readable medium having computer-readable program code stored thereon, the computer-readable program code comprising instructions that when executed by a processor, cause the processor to perform the method of predicting cardiovascular disease (CVD) described herein.

The above and other features will become apparent from the following description and the attached drawings.

BRIEF DESCRIPTION OF THE DRAWINGS

Further aspects of the present disclosure will become apparent from the following description which is given by way of example only and with reference to the accompanying drawings in which.

DETAILED DESCRIPTION

Figure 1:
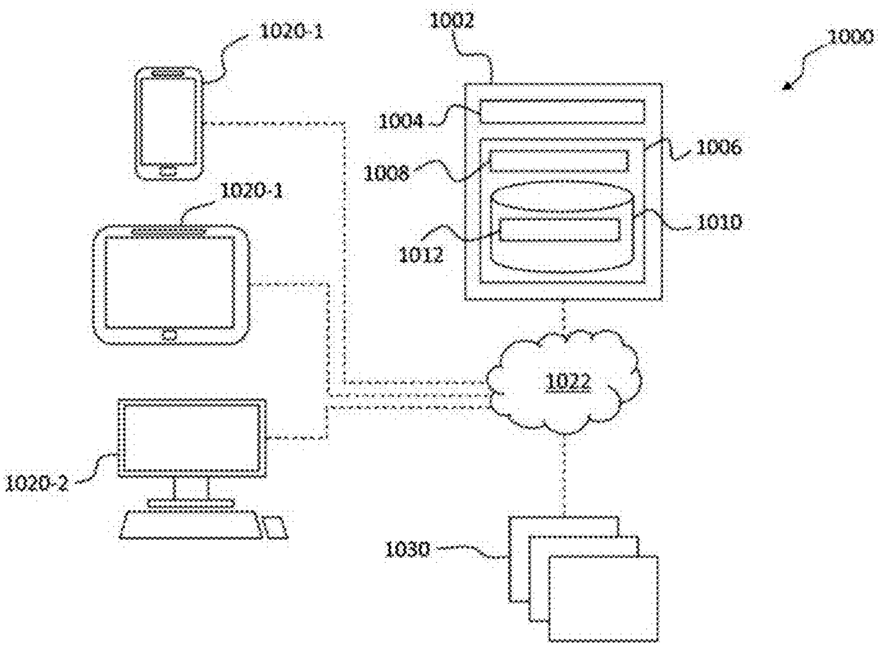
FIG. 1 is a schematic diagram of a system depicting various computing components that can be used alone or together in accordance with aspects of the present technology.

The present technology is generally directed to determining a person's biological age (referred to herein as BioAge) using their retinal photographs (also known as fundus images) and demographic information (e.g., details such as age, gender and ethnicity) with artificial intelligence technology. These images and information may be obtained by optometrists, for example, as part of a routine eye examination.

Biological age is considered a reliable surrogate for the Framingham Risk Score, a tool endorsed by the Heart Foundation for assessing an individual's 10-year risk of experiencing a cardiovascular disease (CVD) event. The BioAge metric is not intended as a replacement for the Framingham Risk Score. However, one key finding by the inventors is that individuals whose biological age was five years older than their chronological age, on average, had Framingham Risk Scores that were twice as high as their peers. Not all people age at the same rate, and as a result there is increasing interest in delineating between an individual's chronological age and their biological age.

While chronological age is defined as the number of years a person has lived, biological age refers to how well the cells in a person's body are aging and functioning. Biological age, therefore, provides a better indicator of life span and future functional capacity. Although differing theories exist to explain this process, it is recognized that the speed at which the cells deteriorate depends broadly upon factors such as the genes we inherit, our lifestyle choices, how much stress we are under and how our bodies respond to infections we get. Work in this area has already revealed that estimates of biological age can more accurately predict mortality or the onset of a broad spectrum of physical and psychological diseases ranging from cardiovascular disease (CVD) to clinically significant depression than chronological age.

In contrast with known tools used to assess biological age, the present technology does not require the collection of data via relatively difficult to access clinical or laboratory assessments (e.g., blood tests and/or radiological tests). The retina has long been recognized as a unique window into an individual's health, as the biomarkers present in retinal images may provide valuable insights into aging, inflammatory health, neurological health, and cardiovascular health. The retinal vasculature allows direct non-invasive visualization of the body's microvasculature, as it is the only part of the body where scientists and clinicians can directly assess the health of an individual's neuro-vascular tissues. While some of these parameters can be evaluated by humans, there are numerous elements that are invisible to the naked eye, but which can be detected by aspects of the present technology.

It is believed that an individual's knowledge of their BioAge may encourage them to live better, healthier lives which will benefit them, their families and their communities. If someone wishes to lower their biological age, there are actions that can contribute to a healthier lifestyle. There is strong evidence that simple interventions that will improve wellbeing, such as losing weight, exercising more, stopping smoking, and ensuring one's blood pressure is under control, may have a significant impact on one's biological age.

FIG. 1 presents a schematic diagram of a system 1000 depicting various computing components that can be used alone or together in accordance with aspects of the present technology. The system 1000 comprises a processing system 1002. By way of example, the processing system 1002 may have processing facilities represented by one or more processors 1004, memory 1006, and other components typically present in such computing environments. In the exemplary embodiment illustrated the memory 1006 stores information accessible by processor 1004, the information comprising instructions 1008 that may be executed by the processor 1004 and data 1010 that may be retrieved, manipulated or stored by the processor 1004. The memory 1006 may be of any suitable means known in the art, capable of storing information in a manner accessible by the processor, comprising a computer-readable medium, or other medium that stores data that may be read with the aid of an electronic device. The processor 1004 may be any suitable device known to a person skilled in the art. Although the processor 1004 and memory 1006 are illustrated as being within a single unit, it should be appreciated that this is not intended to be limiting, and that the functionality of each as herein described may be performed by multiple processors and memories, that may or may not be remote from each other.

The instructions 1008 may comprise any set of instructions suitable for execution by the processor 1004. For example, the instructions 1008 may be stored as computer code on the computer-readable medium. The instructions may be stored in any suitable computer language or format. Data 1010 may be retrieved, stored or modified by processor 1004 in accordance with the instructions 1008. The data 1010 may also be formatted in any suitable computer readable format. Again, while the data is illustrated as being contained at a single location, it should be appreciated that this is not intended to be limiting—the data may be stored in multiple memories or locations. The data 1010 may comprise databases 1012.

In some embodiments, one or more user devices 1020 (for example, a mobile communications capable device such as a smartphone 1020-1, tablet computer 1020-2, or personal computer 1020-3) may communicate with the processing system 1000 via a network 1022 to gain access to functionality and data of the processing system 1002. The network 1022 potentially comprises various configurations and protocols comprising the Internet, intranets, virtual private networks, wide area networks, local networks, private networks using communication protocols proprietary to one or more companies-whether wired or wireless, or a combination thereof. For example, fundus images obtained from one or more fundus imaging devices (herein referred to as a "fundus camera" 1030) may be input to the processing system 1002 via the user devices 1020.

A fundus camera typically comprises an image capturing device, which in use is held close to the exterior of the eye and which illuminates and photographs the retina to provide a 2D image of part of the interior of the eye. Many clinically important regions of the eye may be imaged, comprising the retina, macula, fovea, and optic disc. A single fundus image of a non-dilated eye captures less than 45° of the back of the eye. In practice, a clinician will often choose to capture several photographs while guiding the patients to look up, down, left and right, to create a larger field of view of the retina.

1. First Exemplary Model

Figure 2A:
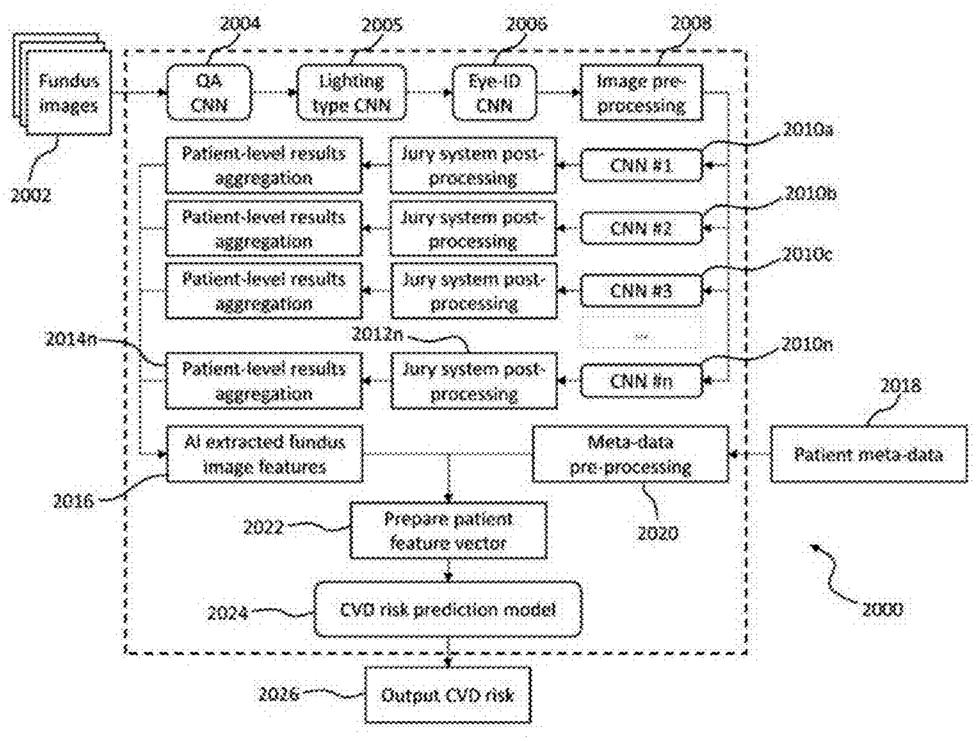
FIG. 2A is a diagram showing a system design describing the flow of processing fundus images to predict a risk of cardiovascular disease (CVD) in accordance with aspects of the present technology.

FIG. 2 illustrates a method/process architecture 2000 for processing fundus images in accordance with aspects of the present technology. For completeness, it will be appreciated that the deep learning models and frameworks disclosed herein are provided by way of example, and that viable alternatives will be apparent to the skilled addressee.

The method 2000 utilises various convolutional neural networks ("CNN"). CNNs are deep learning architectures particularly suited to analysing visual imagery. A typical CNN architecture for image processing consists of a series of convolution layers, interspersed with pooling layers. The convolution layers apply filters, learned from training data, to small areas of the input image in order to detect increasingly more relevant image features. A pooling layer down-samples the output of a convolutional layer to reduce its dimensions. The output of a CNN may take different forms depending on the application, for example one or more probabilities or class labels.

The first dataset for use as training data included measurements from non-diabetic and diabetic patients. Because not all measurements are related to the CVD risk, irrelevant columns were discarded according to the expert advice. As a result, 35 columns corresponding to 21 fields remained, including: age, sex, ethnicity, deprivation score, family history, smoking, systolic blood pressure, BMI, TC/HDL, HbA1c, state of diabetes (Y/N), diabetic type, atrial fibrillation, antihypertensives, antithrombotic medication, lipid lowering medication, eGFR, metolazone prior 6 months, lipids in prior 6 months, LLD prior 6 months, anticoagulation medication prior 6 months, antiplay prior 6 months, CVD event and date, etc. It should be noted that these columns were retained based on the expert's opinion to not miss any helpful variables, but this does not necessitate that all of them should be used in modelling. For the total visits, each patient usually has multiple visits over time (i.e. multiple sets of biometric information may exist for a single patient). Based on expert's advice and to make the study observation time as long as possible, the first visit only for each patient was retained. The resulting first dataset, following the screening process described below, contained 95,992 images from 51,956 patients. A second dataset was created, using the screening process described below, containing 14,280 images from 3,162 patients. This second dataset was used for tuning and validation of the models developed with the training data above.

Figure 3:
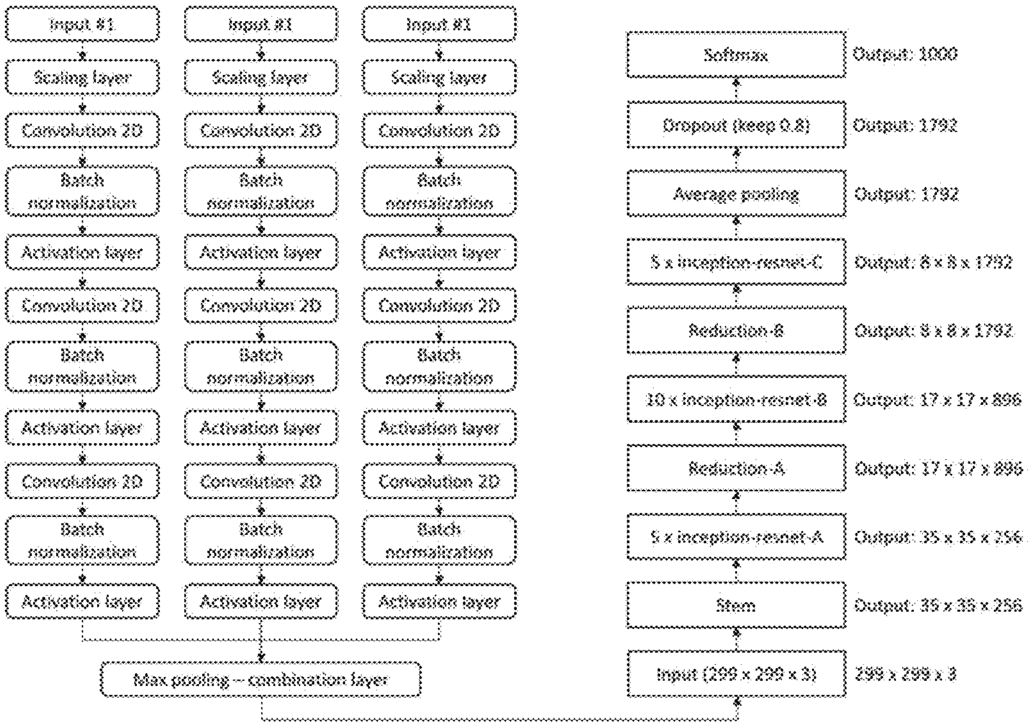
FIG. 3 shows a diagram of an exemplary architecture for a convolutional neural network (CNN) utilised in accordance with aspects of the present technology.

As an example, a modified Inception-ResNet-v2 CNN architecture shown in FIG. 3 may be implemented. Inception-ResNet-v2 is a convolutional neural architecture that builds on the Inception family of architectures but incorporates residual connections. It consists of 164 layers and dozens of inception-residual blocks. Each inception-residual block is made of several parallel branches where different size of convolutional kernel and stride is applied. For example, one branch goes to 1*1 convolutional operation and others go to 1*7, 7*1, 1*3, 3*1, or 3*3. The different size of convolutional kernels intended to capture the image features in the different perspectives. Residual connections are designed to build the deeper network. The idea of residual connection is relatively simple: add the input of each block to the output of the block to preserve the input information. This allows the model to be able to ignore some blocks if necessary and helps the gradients propagation along the network. In examples of the present technology the Inception-ResNet-v2 is used as the feature extractor, and the final layer is adapted to meet the requirements of the present technology, creating a probability of the presence of the learnt feature.

Returning to FIG. 2, at input stage 2002 one or more fundus images are received—for example a collection of fundus photographs of an individual. Quality assurance is performed on the received images to confirm their suitability for further processing. In examples, the quality assurance is performed by a set of one or more quality assurance ("QA") CNNs 2004.

1.1 QA CNNs

The QA CNNs 2004 are trained by inputting sample images previously labelled by an expert clinician, and training them for sufficient iterations. In an example, a QA CNN was based on a modified XCEPTION design (although it is noted that a modified Inception-ResNet-v2 design as described above may be utilised), and trained using a dataset of 20,000 images, wherein the dataset comprised similar proportions of four types of images: Type 1: Eyeballs, rooms or other irrelevant images; Type 2: Severely over-saturated or underexposed images; Type 3: Less than perfect images that could still be useful to a clinician in conducting a manual analysis; and Type 4: High quality images.

Experiments were run in an Intel Xeon Gold 6128 CPU @ 3.40 GHz with 16 GB of RAM memory and a NVIDIA Geforce TiTan V VOLTA 12 GB on Windows 10 Professional. Tensorflow 1.11.0 and Python 3.6.6 were utilised to implement the QA CNN 3004 models.

Hyperparameters comprised: (i) Batch Size: 64. Batch size refers to the number of training samples utilised in one step. The higher batch size, the more memory space need. For an input image size of 320*320, and GPU memory of 12 GB, the batch size was set at 64; (ii) Training\validation\testing split: (70\15\15); (iii) Epoch: 100. One epoch refers to one forward pass and one backward pass of all the training examples; (iv) Learning algorithms: the ADAM optimizer was utilised, being an advanced version of stochastic gradient descent; (v) Initial Learning Rate: 10e-3. Learning rate controls how much model adjusting the weights with respect the loss gradient. Typical learning rates are in the order of [10e-1, 10e-5]. In view of use of the ADAM optimizer and batch normalization, the initial learning rate was initially set at 10e-3; (vi) Loss Function: Softmax Cross Entropy; (vii) Dropout rate: 0.5.

The QA CNN described above achieved 99% accuracy in classifying an input image to the categories. Following training, all of the Type 1 and 2 images were removed. Type 3 images are shown to the clinician, but are not used in further processing. Type 4 images are used as part of further processing.

1.2 Lighting Type CNNs

In examples, one or more Lighting type CNNs 2005 may be configured to determine a device, or characteristic of the device, used to capture the input fundus image. There are two main photography technologies for fundus imaging: a) flash photography, and b) white LED confocal photography, which produce different looking images. Depending on the camera source (and therefore of the image, the subsequent processing (discussed below) is adjusted.

1.3 Eye-ID CNNs

Clinicians often obtain more than one image from a single eye, creating a larger view of the back of the eye. A set of eye-identification (eye-ID) CNNs 2006 are trained to find similarities between several viewpoint images of the same eye, and group them into a single image set. It is important to identify images that belong to the same eye, as a final clinical outcome may be the sum of analysis of each single image in that set.

An exemplary training environment for the eye-ID CNNs 2006 is similar to that described above for the QA CNNs 2004. A database of 160,585 images, from 75,469 eyes of 40,160 people was created. Each image was labelled with Left/Right eye, patient ID (when available) and time stamp of image acquisition. The eye-ID CNNs 2006 were trained on this data set to identify the orientation (Left/Right) of images, and group them based on ID/acquisition time. The trained eye-ID CNNs 2006 achieved more than 99% accuracy. When implemented, the eye-ID CNNs group multiple images submitted by clinician into eye and patient subgroups.

The eye-ID CNNs 2006 are further trained to identify the location of the images on the retina, including identifying the location as being macula-centered or disk-centered.

1.4 Image Preparation

Having been processed by the eye-ID CNNs 2006, the fundus images may also be adjusted before further processing at image preparation stage 2008—for example by performing brightness adjustment and colour balancing for normalisation purposes, and cropping and scaling the images for standardisation.

In an example, a Gaussian filter may be applied to the original fundus photo. An example of such a filter may be expressed as:

$$I_c = \alpha I + \beta G(\rho) * I + \gamma$$

where * denotes the convolution operation, I denotes input image and G(p) represents the Gaussian filter with a standard deviation of ρ. While it will be appreciated that parameters may be optimised for each dataset, an exemplary set of parameters may comprise: alpha=4±1, beta=−4±1, gamma=128±50, ratio=10±10.

1.5 Feature Extraction

Next, good quality images with related labels pass through a plurality of AI models. These AI models include sets of risk contributing factor (RCF) CNNs 2010, to 2010, that are trained to detect indicators of: glycaemic control, blood pressure, cholesterol, and exposure to smoking. These indicators include, but are not limited to: drusen appearance, clustering, and/or location; pigmentation change in density and/or location; arteriovenous crossing; change in arteriovenous crossing calibre and/or thickness change; arteriovenous tortuosity; retinal oedema size and/or pattern; and/or microaneurysms concentration.

Figure 2B:
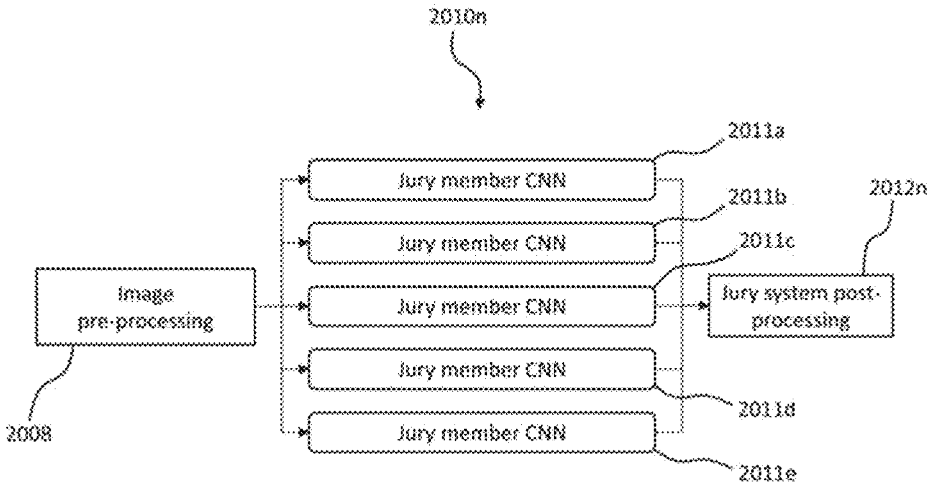
FIG. 2B is a diagram showing a jury model structure of a set of CNNs used in the system in accordance with aspects of the present technology.

The RCF CNNs 2010*a* to 2010, that are looking for signs of glycaemic control, blood pressure, cholesterol, and exposure to smoking in the retina each act as a "jury" system. Referring to FIG. 2B, each RCF CNN 2010 comprises a plurality of jury member CNNs 2011 (in this example, five jury member CNNs 2011, to 2011*e*), each CNN 2011 configured to produce a probability of the feature it is trained to look at (e.g. the existence and concentration of drusens).

In an exemplary implementation of the CNNs 2010, to extract features from fundus images, 101 layers were stacked with residual connections and inception blocks, resulting in 24,276,481 parameters. A dataset of 95,992 images from 51,956 patients was created. Data points recorded for each patient included: Gender, Date of birth, Date of death if applicable, Ethnicity, socioeconomic deprivation index, HbA1c, SCR, TCHDL, ACR, Blood pressure lowering medicine (Y/N), Lipid lowering medicine (Y/N), antithrombotic medicine (Y/N), oral hypos medicine (Y/N), insulin (Y/N), AF, CVD event, CVD event date, EGFR. The dataset was acquired from multiple eye clinics over 15 years, using several different fundus camera models.

For each CNN 2010, the dataset was then split with a ratio of (70%, 15%, 15%) or similar for training, validation and testing respectively. The fundus images were first cropped and resized to 800×800 (or similar) pixel size. The batch size was set to be 6 to gain maximum utilization of GPU memory in training. Adam optimizer was adopted with learning rate 1*10e-3 to update parameters towards the minimization of the loss. Dropout was enabled with rate p=0.2, and the model was trained for at least 100 epochs. This exemplary implementation was done by Python programming language under version 3.7. A cross-entropy loss function was employed to guide the model parameters optimization. The training objective was to minimize the loss function to get the most accurate probability prediction on a CVD event. Typically, cross-entropy loss is utilized in the context of classification problems. However, although the CVD event risk prediction is not a classification task, the label applied was 1 and 0 (representing whether the CVD event happened or not). Therefore, the cross-entropy loss approach was adopted, with the overall loss being formalized as:

$$L = -\frac{1}{H}\left[\sum_{j=1}^{N}[y_j\log(p_j) + (1 - y_j)\log(1 - p_j)]\right]$$

where N is the number of training samples, $y_j$ is the ground truth of sample j, and $p_j$ is the predicted probability of CVD risk for sample j. The model performance is also measured by the cross-entropy.

In jury system post-processing 2012, the outcome of each jury member CNN 2011 is then considered, equally or non-equally weighted compared to the rest of the members, to create a statistical representation of the possibility of the changes observed in the particular fundus image.

After receiving the raw outputs from the CNNs 2010, the output results are aggregated at 2014. For example, for an input fundus image, five juror models give probabilities from 0 to 1, i.e. a minimum of 0 and a maximum of 1 (e.g. a decimal value such as 0.01454), and the probabilities for each grade level across five models are also aggregated. In examples, the output of the models are floating-point numbers and after the aggregation using a mathematical operation (including, but not limited to, weighted mean, min, max, etc.), the final output is still in the form of floating numbers concatenated to form a one-dimensional array (i.e. the individual-level fundus image feature vector) at 2016.

In step 2018, examples, meta-information of an individual associated with the one or more fundus images is received. The meta-information includes gender, ethnicity, HbA1c, TCHDL, etc. Some of the meta-information is categorical data such as gender, ethnicity, deprivation value, medicine, etc, and other is numerical data such as age, HbA1c, etc. The meta-information is pre-processed using standardisation and one-shot encoding. After loading this meta-information into memory, the categorical data is converted to one-hot encoding. For example, 3 bits may be used to represent the gender: [1, 0, 0] means male, [0, 1, 0] is female and [0, 0, 1] stands for others. For numerical biometrics, standardization is applied where each value subtracts its mean and divided by the standard deviation to make sure they have same scale— for example, normal HbA1c values range from 30 to 120, while TCHDL values are usually less than 8. As a further example, numerical features such as age may be standardised to have a mean 0 and standard variance 1. This produces a meta-information vector for the individual.

1.6 CVD Risk Prediction

After the processing pipelines of fundus images 2016 and meta-information 2020 are completed, the individual-level fundus image feature vector and meta-information vector are concatenated together to form an individual feature vector at step 2022. For example, the meta-information vector may be in the form of [0, 1, 0, 0, 1], and the individual-level fundus image feature vector in the form of [0.3, 0.5, 0.4, 0.35, 0.43, . . . ]. The concatenated vector is [0, 1, 0, 0, 1, 0.3, 0.5, 0.4, 0.35, 0.43, . . . ]. This concatenated vector provides a metarepresentation understandable by neural networks.

The individual feature vector is processed by a CVD risk prediction neural network model 2024 utilising a fully connected neural network (FCNN). In examples the FCNN may have at least 5 layers. The size of each layer (i.e. the number of neurons) is 512, 256, 128, 64, 1 respectively. In an exemplary embodiment a ReLU activation function is used at each layer except the last one. The last layer utilizes a sigmoid function to compress the output to be between [0,1] which serves as the predicted risk/probability.

The model is trained using Adam optimizer with the back propagation algorithm, and cross-entropy loss function to depict the predicted value with the target. The training data includes labels for each individual as to whether they encounter a CVD event (e.g., heart failure) after the fundus images been taken and meta-information has been recorded. Therefore, we can measure the AI model predicted risk with the truth using the cross-entropy loss. If an individual had a CVD event, this means the label is 1. The model prediction 0.6 represents a 1-0.6=0.4 error. If the individual never had a CVD event this means the label is 0, and the model prediction 0.2 indicates the error would be |0-0.2|=0.2. Then the average error for each batch is calculated. After having the loss term, the back-propagation method is used to calculate the gradients of each trainable parameter (218,113 parameters in an exemplary model) in terms of the final loss. Then the parameters are updated at the negative gradients direction using Adam algorithm:

$$L = -\frac{1}{m}\sum_{i=1}^{m}(y_i \cdot \log(\hat{y}_i) + (1 - y_i) \cdot \log(1 - \hat{y}_i))$$

The model therefore learns a best set of parameters from the data to minimize the overall loss and gain better prediction results. The relative contribution of each factor toward to the final risk can be estimated using other methods such as controlled experiments. Another method is to "turn on/off" jury member CNNs that are responsible for one aspect (e.g. glycaemic control) and calculate the deviation from the total risk calculated.

In training, a process converts a patient information file into a matrix. The matrix is then converted into a streamed dataset that allows for memory-efficient and time-efficient loading of images. The streamed dataset is then augmented for training purposes. The augmented streamed dataset is then optimized using the gradient descent method via optimizer and loss functions that are provided.

After the pre-processing step, all sorts of available biometrics for each patient are converted to a 1D vector with length 31. Therefore, stacking the feature vector for all patients in the dataset, we will have a feature matrix with shape (44123, 31).

Besides the meta-information, fundus images also need to be pre-processed. After loading the fundus images, the images are re-sized to a pre-defined fixed shape, such as 600*600. Then different image augmentation techniques are employed including randomly adjust brightness, saturation, random flip, rotate, simulate jpeg noise etc.

Because of the large number of images (in an example 95,992 fundus images in total), there are technological limitations preventing loading of all images into memory at once for training. Therefore, the patient's meta-data is transformed with corresponding fundus images into a streamed fashion. In an example, a data generator is created using TensorFlow which produces a mini-batch of data every time. Within each mini-batch, there are several patients visits including the biometrics and fundus images. Then the streamed dataset is fed into the model for training.

The CVD risk prediction neural network model 2024 functions on the underlying recognition that a pattern in a feature of a fundus image (e.g. arterial wall thickening), can be caused for several reasons (i.e. the risk contributing factors such as high blood pressure, high cholesterol, etc)—whether individually or in combination. In other words, one change in the retina cannot be attributed to a single disease, hence the use of probabilities. The 'jury-based' local to global statistical model that represents changes in the retinal photograph is used to estimate a risk for the cardiovascular event within a time period (e.g. 5 to 10 years), and identify the relative contribution of various components of the estimated cardiovascular risk. Here, the jury-based probabilities of the RCF CNNs 2010 are grouped together and assessed against probabilities of changes by non-modifiable factors (e.g. age, race, gender) and modifiable factors (e.g. glycaemic control, blood pressure, cholesterol, and exposure to smoking). In doing so, the CVD risk prediction neural network model 2024 learns if changes to one modifiable factor correlate with changes in other modifiable factors. As an example, in a patient with calculated 20% risk of cardiovascular event in the next 5 years, jury-based estimated probabilities of (i) local changes in arterial wall thickening, and (ii) global colour pattern changes indicate retinal layer thinning, plus probabilities of changes due to age, gender and race are combined to estimate that 8% of the risk are due to non-modifiable factors e.g. (age, race, gender), while from the remaining 12%, 6% is due to high-blood pressure, 3% due to diabetes and the rest split between kidney function and smoking.

1.7 CVD Risk Results Presentation

The end output is a prediction of CVD risk capable of being broken down into the contributing factors, including non-modifiable contributing factors (e.g. based on patient meta-information such as age, gender, and/or ethnicity) and modifiable contributing factors (e.g. based on glycaemic control, blood pressure, cholesterol, and exposure to smoking). In one example, this is achieved by individual or group analysis of the relative contribution of CNNs that are responsible for the effects of each factor (e.g. smoking), including an inclusion/exclusion analysis, weight adjustment analysis, and sensitivity analysis.

2. Second Exemplary Model

Figure 4A:
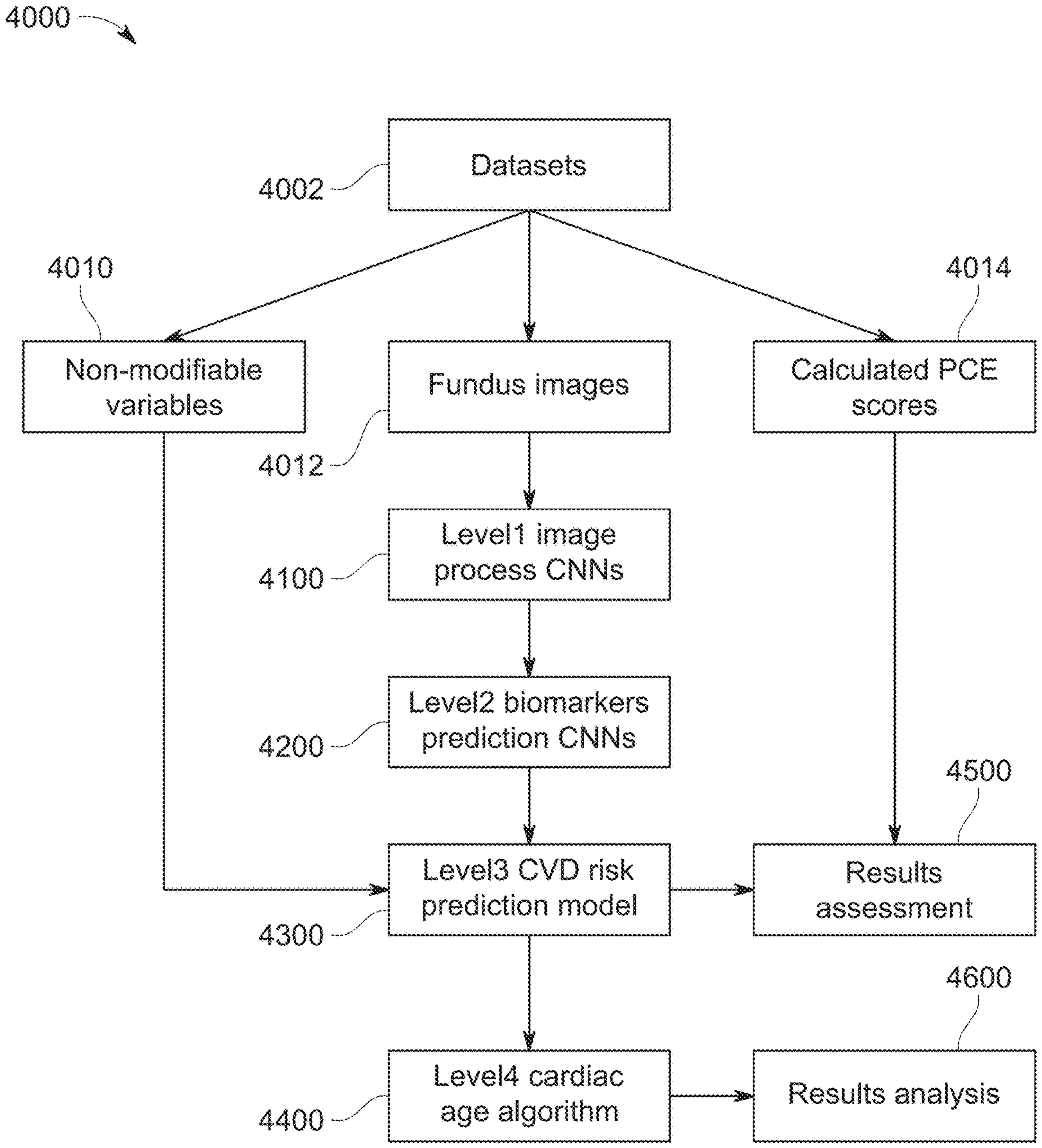
FIG. 4A is a diagram describing another flow of processing fundus images to predict a risk of cardiovascular disease (CVD) and Cardiac BioAge in accordance with aspects of the present technology.

FIG. 4A illustrates a method/process architecture 4000 for processing fundus images in accordance with aspects of the present technology. For completeness, it will be appreciated that the deep learning models and frameworks disclosed herein are provided by way of example, and that viable alternatives will be apparent to the skilled addressee.

Figure 4B:
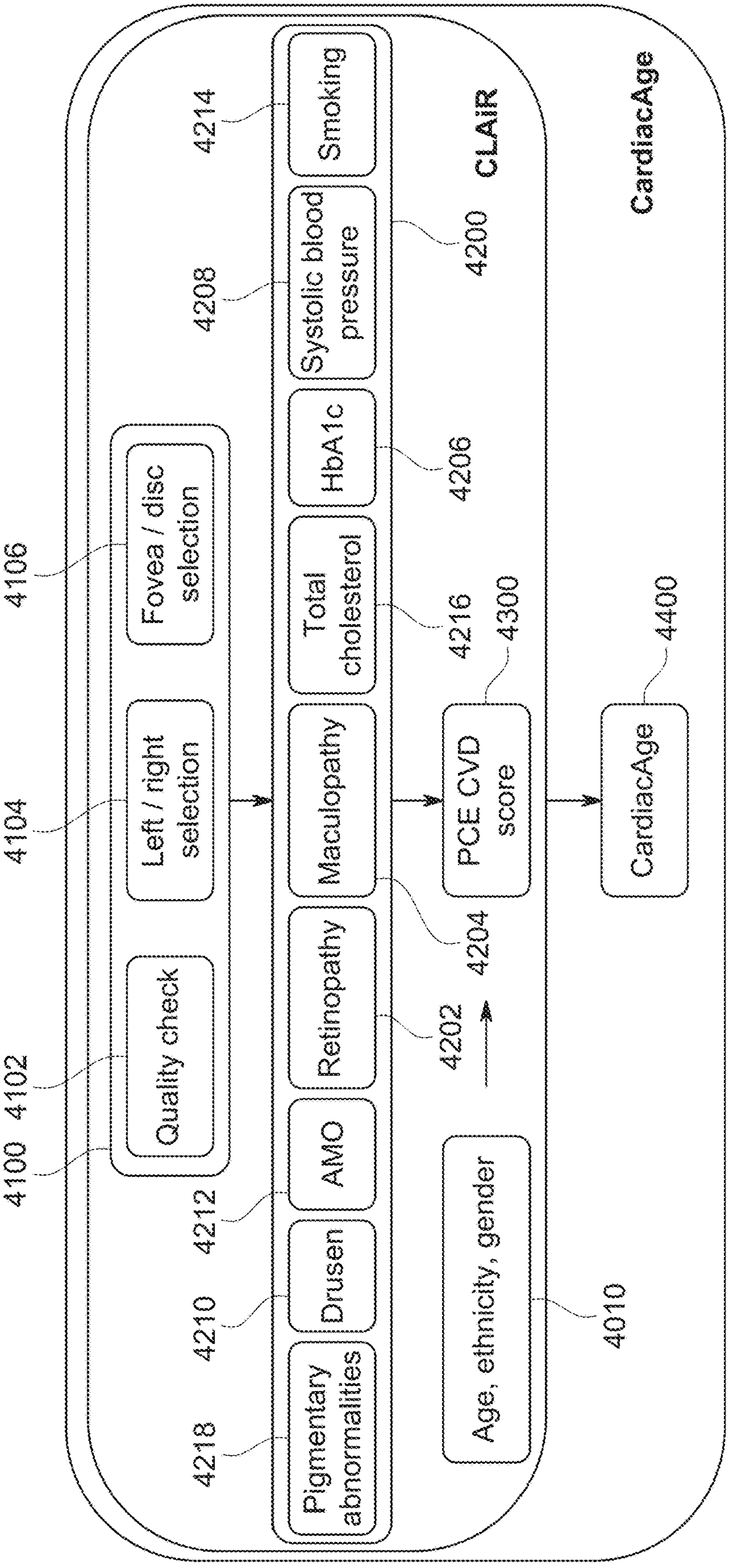
FIG. 4B is a diagram showing a system design for processing fundus images to predict a risk of cardiovascular disease (CVD) and Cardiac BioAge in accordance with aspects of the present technology.

An exemplary model is illustrated in FIG. 4B, comprising four different levels:

2.1 First Level

The first level 4100 includes an image quality control CNN (QC) 4102, a laterality (Left eye/Right eye) detector CNN 4104, and an image location (fovea/non-fovea) detector CNN 4106. The input of this layer is fundus images only. This process ensures that only foveal centered images that are of sufficiently high quality are accepted into the model. Identifying the laterality of the image assists with aggregation of all images of each eye for each individual during the analysis.

2.2 Second Level

The second level 4200 includes nine ensembles of AIs, each consisting of five CNNs (45 in total) which were trained against various labels in the UK BioBank. Each ensemble targeted a unique label in the fundus images: 1. Retinopathy 4202, 2. Maculopathy 4204, 3. HbA1c 4206, 4. Systolic Blood Pressure 4208, 5. Drusen 4210, 6. Age-related macular degeneration (AMD) 4212, 7. Smoking status 4214, 8. Total Cholesterol 4216, and 9. Macular Pigmentation Abnormalities 4218.

These CNNs follow modified versions of the Inception-Resnet-V2 or ResNet50 structures. Taking the single retinopathy CNN model as an example, the model has a deep structure, consisting of 164 layers, and uses a combination of inception and residual blocks. The inception blocks use a combination of convolutional layers with different filter sizes, while the residual blocks use skip connections to enable the model to learn from previous layers. Batch normalization and bottleneck layers are employed to improve training efficiency. Overall, the model architecture is designed to extract features at multiple scales and capture fine-grained details in images, making it well-suited to detect the level of retinopathy or other biomarkers. For each CNN, the dataset was split for training, validation, and testing in 70%, 15% and 15% respectively. The excessive background of the fundus images was cropped, and the resulting image was resized to 800×800 pixels. A batch size of 8 was chosen to optimize GPU memory during training. Adam optimizer was adopted with a learning rate 1*10e-3 to update parameters towards the minimization of the loss. Dropout was enabled with a rate p=0.2, and the model was trained for at least 100 EPOCHs. All codes related to this work were implemented using Python 3.7.

Additionally, a jury system (as descried above) was implemented to arrive at the ultimate prediction for each biomarker. To elaborate using the retinopathy model as an example, there exist six distinct levels of retinopathy (R0-R5). Five jury models are employed to assess each eye, resulting in 30 probability values per eye. These probabilities are merged and consolidated for both eyes, thereby yielding a final value for each patient.

2.3 Third Level

The third level 4300 is a Multi-Layer Perceptron (MLP), which uses the output of the second level CNNs, plus the patient's chronological age, gender, and ethnicity to replicate their Pooled Cohort Equation (PCE) CVD risk score. This PCE CVD risk score is the ground truth label, calculated from nine fields in the UK BioBank dataset for each participant. The architecture of the model comprises an input layer, followed by five dense layers that exhibit a gradual decrease in neuron counts, namely 1024, 512, 256, 128, and 32. These layers are interspersed with batch normalization and LeakyReLU activation functions with a leaky rate of 0.1. To address overfitting concerns, dropout layers with a rate of 0.3 were incorporated after the third, fourth, and fifth dense layers. The ultimate layer, encompassing a single neuron and a linear activation function, predicts the target value. For optimization purposes, an Adam optimizer is utilized with an exponentially decaying learning rate schedule, initialized at **3*e*-3** and decaying by a factor of 0.95 every 1000 steps. The Huber loss function was employed to guide the model parameters updating. To curb overfitting and ensure efficient training, early stopping was implemented.

Shapley Additive Explanations (SHAP) algorithm was used here to elucidate the contributions of each variable to the final prediction of CVD risk. This methodology offers a unified approach for the interpretability in machine learning, fostering a comprehensive and integrative understanding of feature importance in predictive models. Inspired by cooperative game theory, the SHAP values elucidate the equitable distribution of contributions across features for each prediction, thereby facilitating the attribution of each feature's influence on the predicted outcome. In contrast to other local interpretable model-agnostic explanations, SHAP values attribute contributions in a consistent manner, adhering to the principles of local accuracy, missingness, and consistency. This ensures that the cumulative attributions align with the total effect.

2.4Fourth Level

Following the generation of a PCE CVD risk score in the third level, a parameter (Cardiac BioAge) is derived that expresses deviations in CVD risk scores from the norm as a notion of accelerated or decelerated cardiovascular aging in the fourth level 4400. This Cardiac BioAge score is derived for each individual using the following methodology:

The degree of similarity of the individual's predicted CVD risk with the CVD risk score obtained from other similar aged people was determined.

The average (chronological) age of that individuals' closest neighbors, based on the condition of the retina as expressed by multi-dimensional features extracted from the DL models, was determined.

The mean expected age for a person with the individual's predicted CVD risk was determined.

These data were then combined in a probabilistic manner to give a final value for the Cardiac BioAge.

The calculation of Cardiac BioAge can be summarized in the following equation:

$$\text{Cardiac } BioAge_x = P(\text{risk}(x)|x \in X) * \underline{\text{age}(X)} + (1 - P(\text{risk}(x)|x \in X)) * \underline{\text{age}(Y|x \sim Y)}$$

where x refers to the patient, and X is the set of individuals who are in the same age band and gender band as patient x.

The equation broadly has three components:

1. P(risk(x)|x∈X), which is the conditional probability that patient x has CVD risk, risk(x), given that that the patient belongs the set X of individuals who have similar age and gender.
   a. This is estimated using a normal distribution via the following steps:
      1. Calculate the sample mean and standard deviation for predicted CVD risk for set X and constructing a standard normal distribution.
      2. Calculating the Z value for patient x:

$$Z = \frac{\text{risk}(x) - \text{mean}(\text{risk}(X))}{std\ dev_{sample}(\text{risk}(X))}$$

3. Calculating the area of the two tailed survival function for a standard normal distribution using the Z value.
2. <u>age(X)</u>, is the mean age for set X. As the age bins are set to a narrow interval of 1, this value is equivalent to the patient age rounded to the nearest whole number.
3. <u>age(Y|x~Y)</u> is the mean age of patient points who are close to patient x. The implementation consists of these following components: similarity magnitude*cosine similarity age+(1-similarity magnitude)*risk extrapolated age.

2.5 Model Assessment

To assess the accuracy of the AI ensemble to predict an individual's CVD score a comparison was made between the score issued by the AI model with that generated by the PCE equation. Taking a score of ≥7.5% as indicative of an individual as higher-risk, the accuracy of the AI model's ability to predict CVD risk was calculated using the following confusion matrix set out in Table 1 below. The PCE equation outputs were assumed to be the ground truth.

TABLE 2

Establishing the labels for estimating the accuracy of CLAiR in predicting individuals with elevated PCE CVD scores.

| | | |
|---|---|---|
| AI-generated CVD score <7.5% | PCE-generated CVD score <7.5% | True negative |
| AI-generated CVD score <7.5% | PCE-generated CVD score >7.5% | False negative |
| AI-generated CVD score >7.5% | PCE-generated CVD score <7.5% | False positive |
| AI-generated CVD score >7.5% | PCE-generated CVD score >7.5% | True positive |

This confusion matrix was then used to calculate the accuracy, sensitivity and specificity of the overall model.

Figure 5A:
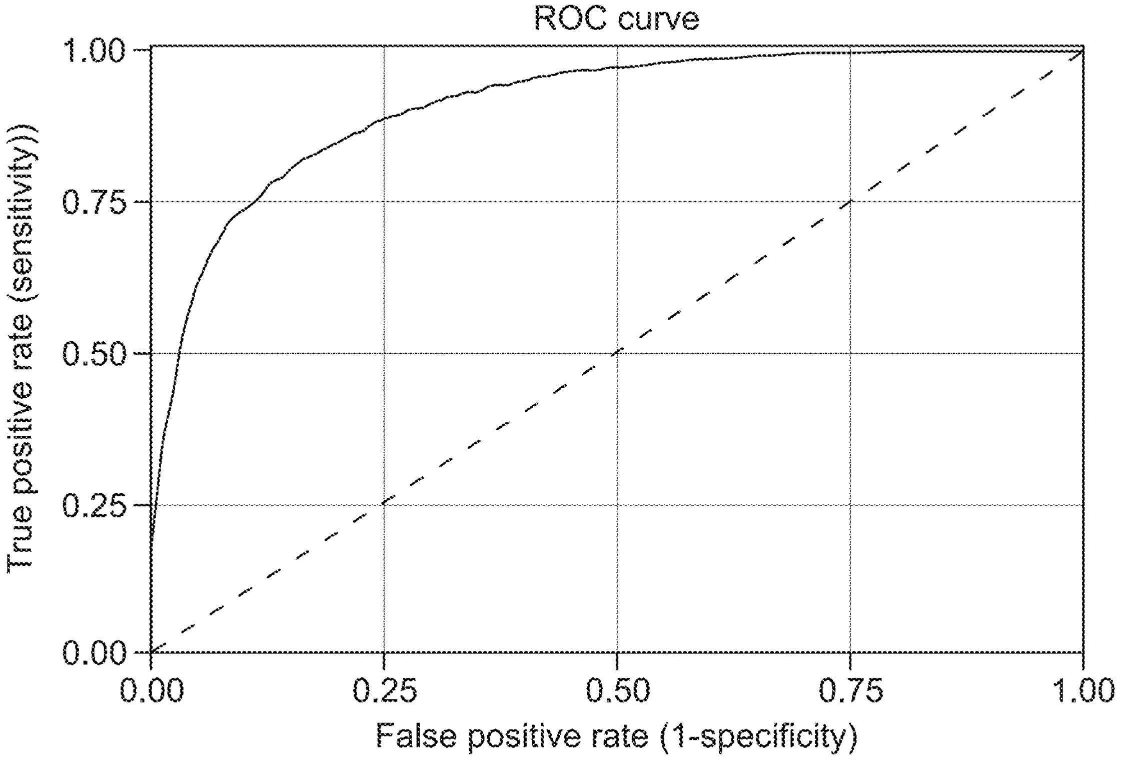
FIG. 5A shows a receiver operating characteristic (ROC) curve for the model used to predict the risk of CVD in accordance with aspects of the present technology.
Figure 5B:
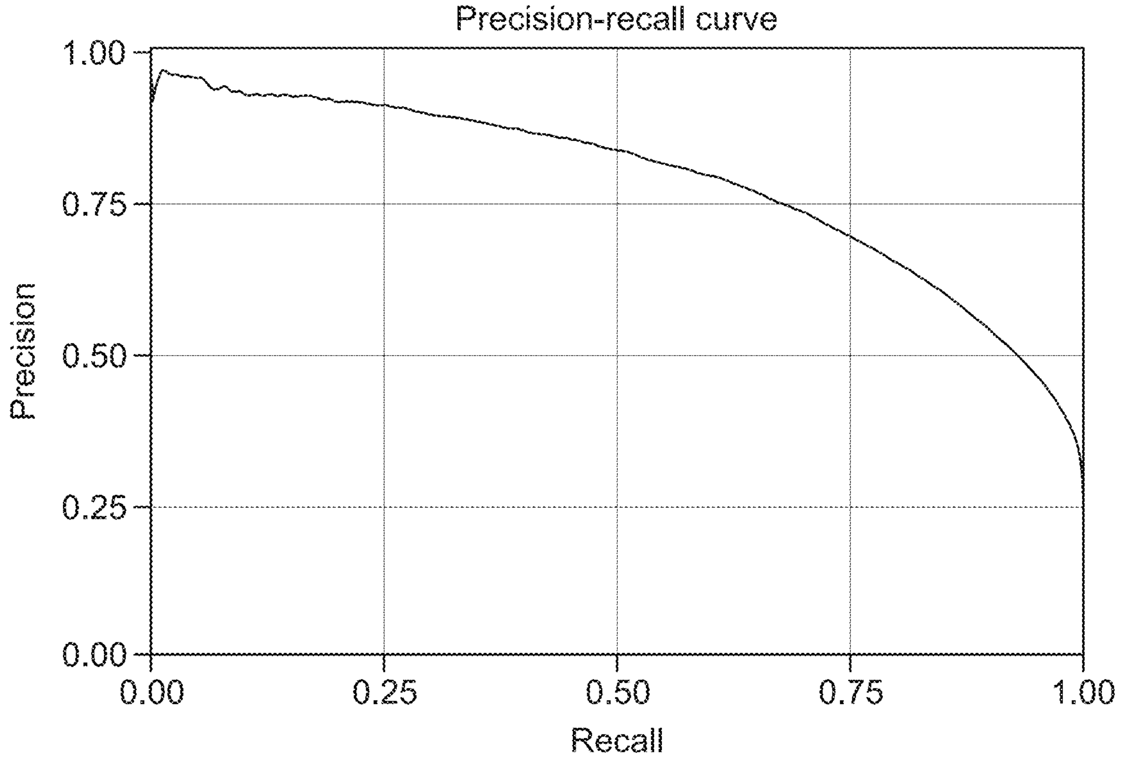
FIG. 5B shows a Precision-Recall curve for the model used to predict the risk of CVD in accordance with aspects of the present technology.

The ability of the model to identify high risk individuals (PCE-generated CVD score >7.5%), compared to those produced by the PCE equation is shown in Table 2. Identifying higher-risk individuals, our model achieved ROC AUC: 88.6%, Sensitivity: 83.7%, Specificity: 90.2% on test set. The ROC and the accompanying Precision recall F1 curve plots are shown in FIGS. 5A and 5B.

TABLE 2

Confusion matrix comparing the CLAiR generated PCE score v equation PCE calculated CVD scores.

| | PCE-generated CVD score <7.5% | PCE-generated CVD score >7.5% |
|---|---|---|
| CLAiR generated CVD score <7.5% | 5923 | 331 |
| CLAiR generated CVD score >7.5% | 642 | 1710 |

To test the validity of the Cardiac BioAge generated by the Level 4 outputs the UK BioBank dataset was divided into several chronological age brackets [40-43, 43-46, 46-49, 49-52, 52-55, 55-59, 59-62, 62-65, 65-68, 68-72, 72-75]. Note that the oldest subgroup was deliberately chosen to be wider (10 year gap) to ensure enough participants would be available in this age bracket. For each chronological age bracket the AI model produced a range of Cardiac BioAge values. A key tenet in the concept of Cardiac BioAge is that the biometric of a group of individuals of a given chronological age will normally distributed around the chronological age. Those individuals whose Cardiac BioAge is older than their chronological age thus represent a cohort of individuals whose cardiovascular systems are aging more rapidly than would be expected. Conversely those individuals whose Cardiac BioAge is younger than expected represent a cohort of individuals who are aging more slowly than would be expected. In each age bracket, individuals whose Cardiac BioAge was more than 5 years greater than their actual age (i.e., Cardiac BioAge—Chronological Age>5) were arbitrarily defined as individuals with "accelerated aging" for that chronological age group.

To test the validity of the Cardiac BioAge produced by the model, biomarkers were compared that are known to be associated with cardiac ageing (CVD risk, HbA1c, Systolic BP) in the cohort of "accelerated aging" individuals compared to their chronological peers. The hypothesis was that if the cohort of individuals who are on an accelerated aging path should have significantly worse values of these biomarkers compared to their peers.

Figure 6:
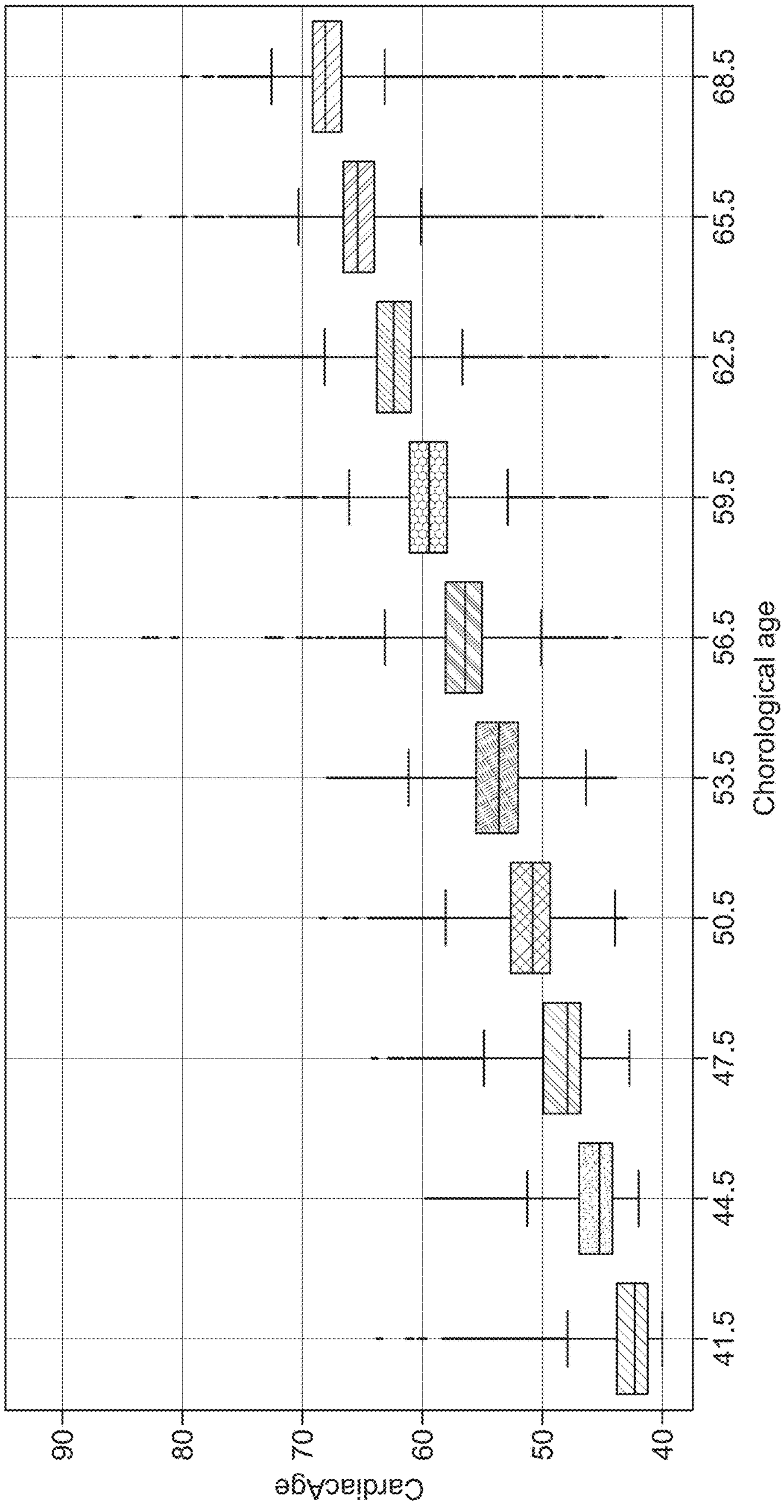
FIG. 6 shows a box and whiskers plot showing the spread of Cardiac BioAge values obtained at each chronological age bracket, as predicted in accordance with aspects of the present technology.

The spread of Cardiac BioAge values obtained at each chronological age bracket is illustrated in FIG. 6.

To study the efficacy of Cardiac BioAge to identify individuals with "accelerated cardiac aging", the mean of the PCE 10-year CVD risk, HbA1c, Systolic BP and total cholesterol were calculated for each age bracket. The means of the same datasets were then calculated separately within each age bracket for: a) Those individuals with "accelerated aging" (i.e. Cardiac BioAge—age>5), and b) All others (i.e. Cardiac BioAge≤5).

Having established the mean of these data points for the cohort of accelerated agers and the remainder, the differences from the overall mean from the entire cohort of each age group were calculated: (e.g. $\mathrm{Mean}_{Blood\ Pressure\ 40\text{-}43YO}-\mathrm{Mean}_{Blood\ Pressure\ 40\text{-}43YO\ accelerated\ aging}$ vs $\mathrm{Mean}_{Blood\ Pressure\ 40\text{-}43YO}-\mathrm{Mean}_{Blood\ Pressure\ 40\text{-}43YO\ others}$). These deviations from the age matched means for people with "accelerated aging" and others were then compared, using a paired t-test. As shown in Table 3, in all age bands and for both genders the mean scores for PCE 10-year CVD risk, HbA1c and Systolic BP derived from the accelerated agers were statistically significantly higher than the mean scores derived from the rest. The exception was total cholesterol, where for all age groups and both genders the scores derived from the cohort of accelerated agers were statistically significantly lower than the rest.

TABLE 3

PCE 10-year CVD risk, HbA1c, Systolic BP and total cholesterol differences among those with accelerated aging (Cardiac BioAge-age >5) and the others

| field name | Difference from age group mean (accelerated agers) | N patients (accelerated agers) | Difference from age group mean (others) | N patients (others) | Paired t-test statistic | t-test p-value |
|---|---|---|---|---|---|---|
| systolic blood pressure (mmHg) | 4.2 (16) | 201 | −0.2 (15.4) | 4911 | 3.832 | 0.0002 |
| HbA1c (mmol/mol) | 3.5 (7.6) | 163 | −0.1 (5.5) | 4409 | 5.985 | 0 |
| PCE CVD score (%) | 0.7 (2.9) | 201 | −0.02 (3.3) | 4911 | 3.267 | 0.0013 |
| Total Cholesterol (mg/dL) | −0.2 (1.0) | 201 | 0 (1.1) | 4911 | −2.514 | 0.0126 |

The results demonstrate that the present technology can reliably detect those individuals with intermediate and high risk PCE CVD scores using only the retinal image, and the individuals age, ethnicity, and gender with a ROC AUC of 88.6%, a sensitivity of 83.7% and a Specificity of 90.2%. To date, developers of DL algorithms designed to predict CVD risk have reported the performance of their model as an AUC statistic, with successful model being accepted as one that achieves an AUC>0.70. Although this approach has its merits, merely knowing that a model can predict CVD risk with an AUC>0.70 is of limited value because of the tendency of biometric data to be normally distributed. If the biometric data is tightly clustered around the mean, then a high level of accuracy can be achieved if the model has done nothing more than learn the mean datapoint. A high level of accuracy therefore does not necessarily mean that the algorithm has learnt what was expected and to be sure that an algorithm is performing then arguably the outputs need to be both biologically plausible and clinically meaningful. In the present technology a Multi-Layer Perceptron (MLP) is utilised to derive the final predicted PCE CVD risk score. Consequently, a determination may be made as to the magnitude of the attribution factor allocated to each component variable that comprised the individuals PCE score by deriving the Shaply value. The advantage of this approach is that it allows for display of the relative contributions of the component risk factors on the PCE risk score generated for each individual. This not only allows physicians to gain a better understanding of the relative important of these component risk factors for their individual patients, but it also allows them to open the "black box" and gain a better understanding of how the model arrived at its results, affording them a mechanism to test its plausibility.

Although the baseline CVD risk increases with age, the actual likelihood of a CVD event also varies between individuals of the same chronological age. Individuals age at different rates, which impacts both the risk of an individual developing a chronic disease and the severity to which they are impacted by it. That individuals age at different rates is not captured by traditional regression-based risk equations as they assume all individuals in the population age at the same rate. As a result, they are relatively insensitive to the variation in individual risk that results from biological aging.

Aspects of the present technology also allows for identification of individuals who have an accelerated CVD risk profile when compared to their chronological peer group. Having produced the PCE cardiac risk score for all individuals, the mean expected age for a person with any given individual predicted CVD risk is determined by a clustering method (this metric designated herein as an individual's Cardiac BioAge). Once the individual's Cardiac BioAge has been determined this value may then be compared to their actual chronological age. The difference between their chronological age and the Cardiac BioAge thus generates an "age gap". Compared to their chronological peers, individuals whose age gap was >5 years, have CVD risk scores, a systolic blood pressure, and HbA1c that are significantly higher across both genders. The total cholesterol was significantly lower. These data suggest that aspects of the present technology was able to not only able to accurately predict CVD within a population but was also able to extract data from the retinal fundus that can identify those individuals whose cardiac risk profile is significantly "older" compared to their peers.

3. Cardiac BioAge and AgeGap

A further model training and assessment was undertaken as described herein. The UK Biobank was used for training and internal validation. The validation subset represented 20% of the data, selected randomly prior to development. The data from the UK Biobank can be accessed via a direct request to the UK Biobank (IRB UOA-86299); and was obtained using approved data management and data transfer protocols. 89,894 fundus images from 44,176 unique participants from the UK Biobank were used in this study. Participants in the UK Biobank were recruited from a UK general population with only approximately 5% of the UK Biobank population self-identified as having diabetes "diagnosed by doctor".

The 10K dataset from the US-based EyePACS study, with multiple differences from UK Biobank, was used for external validation (IRB UCB 2017-09-10340). The dataset used for this analysis (EyePACS 10K) consisted of a subset of 8,969 individuals who had sufficient clinical data to calculate a traditional PCE risk score. Of these, 978 were excluded as they had established CVD prior to the date of retinal imaging. The external validation dataset thus comprised 18,900 retinal images from 7,861 individuals. The composition of datasets used in this study is shown in Table 4.

TABLE 4

The demographic and risk factor makeup of the UK Biobank derived training and internal test datasets and the EyePACS 10K external validation dataset used in this study. Significance test was performed between UK Biobank training and test, as well as Biobank training and EyePACS 10K external validation (* P < 0.01 z test. **P < 0.001 z test. † P < 0.01 Chi square). The UK Biobank did not include Hispanic ethnicity as an option and the White participants were predominantly of British and Irish origin. EyePACS 10K included choices of Hispanic, Black, or White, so separating Hispanic Black participants from Hispanic White participants was not possible.

| | UK Biobank: Training N = 35,570 | | UK Biobank: Test N = 8,606 | | EyePACS 10K N = 7,861 | |
|---|---|---|---|---|---|---|
| | Mean | Std | Mean | Std | Mean | Std |
| Age (years) | 56 | 8 | 57 | 8 | 57.0 | 7 |
| Systolic Blood Pressure (mmHg) | 134 | 18 | 134* | 17 | 131** | 12 |
| Diastolic Blood Pressure (mmHg) | 81 | 10 | 81** | 9 | 71** | 8 |
| HbA1c (%) | 5.4% | 0.6% | 5.4%** | 0.5% | 8.1%* | 1.7% |
| Total cholesterol(mg/dL) | 220 | 44 | 219** | 43 | 179** | 43 |
| HDL cholesterol(mg/dL) | 58 | 15.1 | 58** | 15 | 46** | 12 |
| BMI | 27 | 4 | 27 | 4 | Not known | Not Known |
| Sex at birth | Male 16,313 (46%) | Female 19,257 (54%) | Male 3,991 (46%) | Female 4,615 (54%) | Male 3,191 (40%) | Female 4,670 (59%) |
| Current Smoker | TRUE 4,526 (13%) | FALSE 29,535 (87%) | TRUE 1,100 (13%)† | FALSE 7,122 (87%) | TRUE 465 (6%)† | FALSE 7,396 (94%) |
| Diabetes (%) | 5% | | 4% | | 99% | |
| Race/Ethnicity | Non-Hispanic White | 93% | Non-Hispanic White | 93% | Non-Hispanic White | 5% |
| | Asian without Chinese | 2% | Asian without Chinese | 2% | Asian | 6% |
| | Chinese | <1% | Chinese | <1% | Asian sub-continent | <1% |
| | Black | 2% | Black | 2% | Black | 7% |
| | Hispanic | N.A. | Hispanic | N.A. | Hispanic | 65% |
| | Mixed | <1% | Mixed | <1% | Mixed | 0% |
| | Other | 1% | Other | 1% | Other | % |
| | Prefer not to answer | <1% | Prefer not to answer | <1% | Prefer not to answer | <1% |

TABLE 4-continued

The demographic and risk factor makeup of the UK Biobank derived training and internal test datasets and the EyePACS 10K external validation dataset used in this study. Significance test was performed between UK Biobank training and test, as well as Biobank training and EyePACS 10K external validation (* P < 0.01 z test. **P < 0.001 z test. † P < 0.01 Chi square). The UK Biobank did not include Hispanic ethnicity as an option and the White participants were predominantly of British and Irish origin. EyePACS 10K included choices of Hispanic, Black, or White, so separating Hispanic Black participants from Hispanic White participants was not possible.

| | | | | | |
|---|---|---|---|---|---|
| Do not know | <1% | Do not know | <1% | Do not know | 13% |

Further, the level of diabetic retinopathy was extracted from the EyoPACS 10K dataset and the highest severity of retinopathy observed across both eyes was recorded (see, Table 5).

TABLE 5

Distribution of diabetic retinopathy grades in the EyePACS 10K dataset. R0 = No DR, R1 Mild Non-proliferative diabetic retinopathy in one eye only, R1+ Mild NPDR in both eyes, R2 Moderate NPDR, R3, Severe NPDR, R4 Proliferative DR.

| Diabetic Retinopathy Severities | EyePACS 10K (N = 7,861) |
|---|---|
| R0 | 5,760 |
| R1 | 343 |
| R1+ | 235 |
| R2 | 1,017 |
| R3 | 205 |
| R4 | 152 |
| No Values Entered | 149 |

In this example, the inclusion criteria included: a person with data in the dataset with demographics that include age, gender and ethnicity, at least one image of good quality from each eye, and information on CVD risk factors (e.g., Systolic Blood Pressure, HbA1c, Total Cholesterol, HDL Cholesterol).

In this example, the inclusion criteria included: a person who was younger than 40 or older than 75 at the time of retinal imaging; a person who was pregnant at the time of retinal imaging; a person who is known to have had a previous cardiac event, such as a stroke or heart attack prior to the retinal imaging; a person who is noted in the dataset as having (in one or both eyes, at the time of retinal imaging): persistent vision impairment, congenital eye disease, or severe ocular trauma.

3.1 Model Assessment

Individuals in each dataset were divided into discrete age bands by decade of life and the Cardiac BioAge generated. To validate the output of the deep learning model an individual's AgeGap (Cardiac BioAge—chronological age) was calculated. Individuals within each age cohort were ranked in quartiles from the highest to the lowest AgeGap and the profile of the CVD risk biomarkers, in this example systolic blood pressure (SBP), HbA1c, and total cholesterol/HDL ratio (TChol/HDL) were then compared in those in the top and bottom quartiles of AgeGap. Finally, for those people living with diabetes a similar calculation was performed to compare the presence of, and severity of any diabetic retinopathy (DR). The following statistical analyses were performed and reported:

Linear regression between BioAge and chronological age.

Report: R2, slope, intercept

Plot: Scatter plot of BioAge vs. chronological age.

Comparison of the biomarker profile of individuals issued with an AgeGap in the top quartile of their age cohort (Top 25% individuals with the highest AgeGap) compared to those individuals issued with an AgeGap in the bottom quartile of their age cohort (bottom 25% of individuals with the lowest AgeGap) for:

Systolic BP

HbA1c

Total cholesterol/HDL ratio

The presence of any diabetic retinopathy in the EyePACS 10K dataset (noting that if the diabetic retinopathy was asymmetrical then the highest grade across both eyes was used).

10 year CVD risk as defined by the Pooled Cohort Equation (PCE).

Figure 7A:
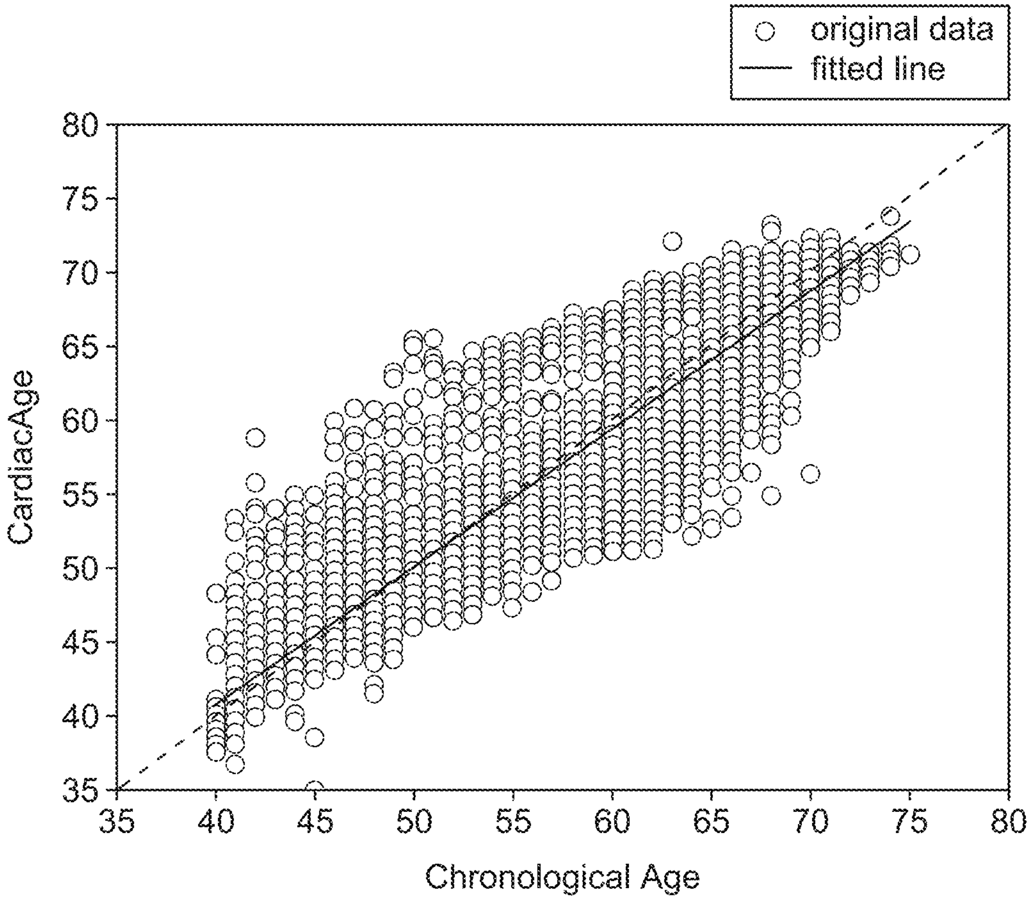
FIG. 7A shows a distribution of Cardiac BioAge vs chronological age in a first dataset in accordance with aspects of the present technology.
Figure 7B:
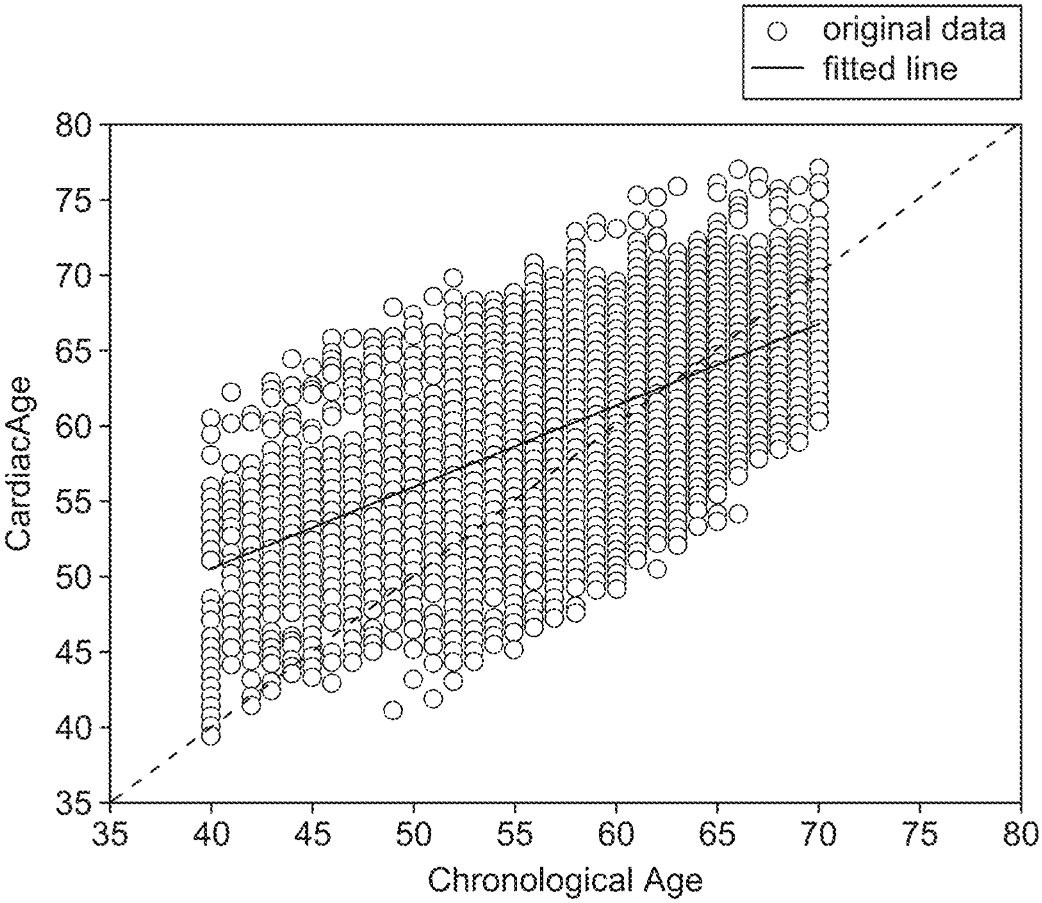
FIG. 7B shows a distribution of Cardiac BioAge vs chronological age in a second dataset in accordance with aspects of the present technology.

The correlation between the predicted Cardiac BioAge and the chronological age for individuals in both the UK Biobank and EyePACS 10K datasets is illustrated in FIGS. 7A and 7B respectively. FIG. 7A shows distribution of Cardiac BioAge vs chronological age in the UK Biobank dataset (R-squared: 0.89, slope: 0.93, intercept: 3.38). FIG. 7B shows distribution of Cardiac BioAge vs chronological age in the EyePACS 10K dataset (R-squared: 0.51, slope: 0.54, intercept: 29).

In the internal validation UK Biobank dataset the mean Cardiac BioAge was very close to the recorded chronological age in all age groups (R-square 0.89). In contrast the mean Cardiac BioAge in the external validation EyePACS 10k dataset was markedly elevated compared to the chronological age for all age groups under 62. Thereafter the mean Cardiac BioAge was similar to, and in the older age groups, less than the chronological age (R-square 0.51). The magnitude of the difference between the Cardiac BioAge and chronological age was greatest in younger patients and decreased sequentially through until the early 60's.

Individuals within both the UK Biobank internal validation dataset and the EyePACS 10K external validation datasets were grouped into three categories by decade of life; 40-50, 50-60, 60-70. Within each age cohort the AgeGap of each individual was derived and the cohort was then arranged into ascending quartiles, with those with the highest AgeGap being grouped in the top quartile, and those with the lowest AgeGap being grouped in the bottom quartile. The mean (and standard deviation) of the following cardiac biomarkers was then assessed: SBP, HbA1c, TChol/HDL ratio, 10-year CVD.

In both the internal and external validation datasets, within nearly all age cohorts, the mean HbA1c, and the mean SBP, were significantly higher in those individuals in the top quartile of the age cohort distribution, compared to those individuals in the bottom quartile of the age cohort distribution (see Tables 6-9]. A similar trend was also seen in the results for total TChol/HDL ratio in the UK Biobank, but there was no significant difference in the TChol/HDL ratio in any of the age cohorts in the EyePACS 10K dataset (see Tables 10 and 11).

TABLE 6

Mean and standard deviation [mean (std)] of HbA1c (%) measurements, for the highest 25% vs lowest 25% of AgeGap participants at every age decile in the UK Biobank

| Age Group | HbA1c of the top quartile | HbA1c of the bottom quartile | Number in group | p-value |
|---|---|---|---|---|
| 40-50 | 5.3% (0.5) | 5.2% (0.4) | 240 | <0.001 |
| 50-60 | 5.5% (0.6) | 5.3% (0.5) | 809 | <0.001 |
| 60-70 | 5.6% (0.7) | 5.5% (0.5) | 793 | <0.001 |

TABLE 7

Mean and standard deviation [mean (std)] of HbA1c (%) measurements, for the highest 25% vs lowest 25% of AgeGap participants at every age decile in the EyePACS 10K

| Age Group | HbA1c of the top quartile | HbA1c of the bottom quartile | Number in group | p-value |
|---|---|---|---|---|
| 40-50 | 8.9% (2.0) | 8.3% (1.8) | 342 | <0.001 |
| 50-60 | 8.8% (1.9) | 7.9% (1.6) | 789 | <0.001 |
| 60-70 | 8.2% (1.6) | 7.5% (1.3) | 796 | <0.001 |

TABLE 8

Mean and standard deviation [mean (SD)] of systolic blood pressure (mmHg) measurements, for the highest 25% vs lowest 25% of AgeGap participants at every age decile in the UK Biobank

| Age Group | Systolic blood pressure of the top quartile | Systolic blood pressure of the bottom quartile | Number in group | p-value |
|---|---|---|---|---|
| 40-50 | 128 mmHg (15) | 121 mmHg (13) | 518 | <0.001 |
| 50-60 | 137 mmHg (17) | 125 mmHg (15) | 672 | <0.001 |
| 60-70 | 141 mmHg (17) | 131 mmHg (15) | 918 | <0.001 |

TABLE 9

Mean and standard deviation [mean (SD)] of systolic blood pressure (mmHg) measurements, for the highest 25% vs lowest 25% of AgeGap participants at every age decile in the EyePACS 10K

| Age Group | Systolic blood pressure of the top quartile | Systolic blood pressure of the bottom quartile | Number in group | p-value |
|---|---|---|---|---|
| 40-50 | 128 mmHg (12) | 126 mmHg (11) | 343 | 0.18 |
| 50-60 | 132 mmHG (13) | 129 mmHg (12) | 792 | <0.001 |
| 60-70 | 135 mmHg (14) | 132 mmHg (12) | 799 | <0.001 |

TABLE 10

Mean and standard deviation [mean (SD)] of TChol/HDL measurements, for the highest 25% vs lowest 25% of AgeGap participants at every age decile in the UK Biobank

| Age Group | Total cholesterol/ HDL ratio of the top quartile | Total cholesterol/ HDL ratio of the bottom quartile | Number in group | p-value |
|---|---|---|---|---|
| 40-50 | 3.9 (1.0) | 4.0 (1.1) | 518 | 0.18 |
| 50-60 | 4.1 (1.0) | 3.8 (1.1) | 672 | 0.02 |
| 60-70 | 4.1 (1.0) | 3.8 (1.0) | 918 | 0.02 |

TABLE 11

Mean and standard deviation [mean (SD)] of TChol/HDL ratio measurements, for the highest 25% vs lowest 25% of AgeGap participants at every age decile in the EyePACS 10K

| Age Group | Total cholesterol/ HDL ratio of the top quartile | Total cholesterol/ HDL ratio of the bottom quartile | Number in group | p-value |
|---|---|---|---|---|
| 40-50 | 4.4 (1.3) | 4.6 (1.7) | 343 | 0.06 |
| 50-60 | 4.1 (1.3) | 4.2 (1.3) | 792 | 0.2 |
| 60-70 | 3.8 (1.2) | 3.7 (1.1) | 799 | 0.12 |

Figure 8:
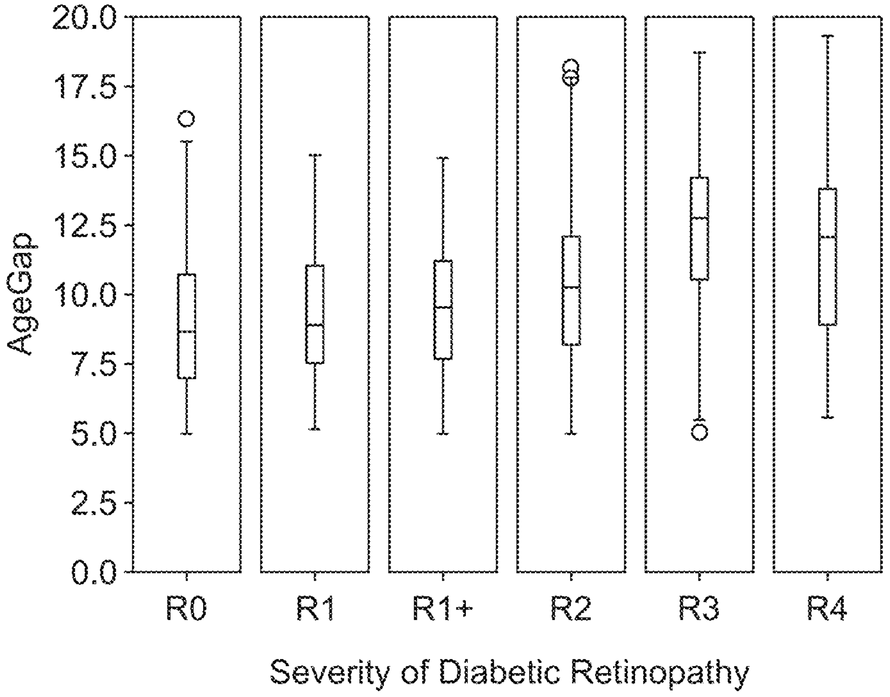
FIG. 8 shows a box and whiskers plot showing the relationship between severity of diabetic retinopathy and AgeGap in accordance with aspects of the present technology.

In the EyePACS 10K dataset diabetic retinopathy grades were also available. When the percentage of individuals with diabetic retinopathy in the two quartiles was examined, individuals whose AgeGap was in the top quartile of the age cohort distribution had significantly higher prevalence rates of diabetic retinopathy compared to those individuals in the bottom quartile (see, Table 12). Increasing severity of diabetic retinopathy was associated with an incremental increase in the observed AgeGap for all categories except for proliferative diabetic retinopathy (see R4; FIG. 8: Relationship between severity of diabetic retinopathy and AgeGap in the EyePACS dataset), (F-value=168, p-value=<0.001).

TABLE 12

Presence of any level of diabetic retinopathy, for the highest 25% vs lowest 25% of AgeGap participants at every age decile in the EyePACS 10K dataset (given as % with DR).

| Age Group | Presence of any Diabetic retinopathy in the top quartile | Presence of any Diabetic retinopathy in the bottom quartile | p-value |
|---|---|---|---|
| 40-50 | 35% | 14.6% | 0.01 |
| 50-60 | 54% | 9.2% | <0.01 |
| 60-70 | 96% | 7.5% | <0.01 |

Once the individual's Cardiac BioAge had been determined this value was then compared to their actual chronological age. The difference between the individuals chronological age and their Cardiac BioAge thus generated was the "AgeGap". Compared to their chronological peers and when grouped by decades of life, individuals with an AgeGap in the top quartile of each age cohort had significantly higher SBP and HbA1c, than those individuals with an AgeGap in the bottom quartile of most age cohorts in both the internal and external validation datasets. The data for TChol/HDL was less clear. Over 70% of individuals over the age of 50, in both the top and bottom AgeGap quartiles in the EyePACS dataset were on a statin. In comparison only 20% of high-risk older patients in the UK Biobank were taking one.

The inventors found that there was a correlation with chronological age and Cardiac BioAge in both datasets, but the strength of this correlation was stronger in the UK Biobank compared to EyePACS 10K dataset (R squared 0.89 v 0.51; slope 0.93 v 0.54: UK Biobank v EyePACS 10K. The DL model was able to discern a trend that, at least at a population level, people living with diabetes are on an accelerated aging curve compared to their non-diabetic counterparts. Compared to their non-diabetic peers, in every age band up, individuals in the EyePACS 10K dataset had significantly higher Cardiac BioAge, and thus higher AgeGap, than those in the UK Biobank. The DL model was able to discern that younger people living with diabetes in the EyePACS 10K dataset had markedly worse AgeGap when compared to older people living with diabetes.

One of the components of the suite of DL models that comprises the Cardiac BioAge DL model is a DR feature detector that has been independently trained to grade diabetic retinopathy. Review of the EyePACS 10K data reveals that the DR feature detector is clearly being activated. In the top quartile of AgeGap, less than 47% had R0, and the rest had R2 or worse. In comparison, in the bottom quartile of AgeGap, more than 88% of people had R0 but only 5% had R2 or worse (see, Table 13).

TABLE 13

Prevalence of diabetic retinopathy in the EyePACS 10K dataset, in each age bracket and their top and bottom Cardiac BioAge quartile

| Age | R0 | | ≥R2 | |
|---|---|---|---|---|
| Group | Top quartile | Bottom quartile | Top quartile | Bottom quartile |
| 40-50 | 48% | 82% | 45% | 9% |
| 50-60 | 44% | 90% | 51% | 5% |
| 60-70 | 48% | 93% | 43% | 2% |

The inventors found that the presence of any DR was associated with a significantly higher AgeGap compared to individuals with no DR in all age cohorts (see, Table 12). They also found that apart from Proliferative diabetic retinopathy where the Cardiac BioAge gap was similar to those with Severe Non Proliferative DR, the AgeGap increased sequentially with the severity of an individual's retinopathy where diabetic retinopathy was present (see, FIG. 8).

The study externally validates the Cardiac BioAge model, designed to detect individuals who have a higher cardiovascular risk factors compared to their peers based on nothing more than a retinal photograph and limited demographic data. The study further demonstrates that within a high risk population of people living with diabetes, the DL model appears to be able to further stratify risk based on the presence of absence of DR.

4. Cardiac BioAge and Comparison to Leucocyte Telomere Length

Studies have reported an inverse associate between CVD events, risks, and hypertension, and the biological marker Leukocyte telomere length (LTL). A comparison of the Cardiac BioAge metric of the present technology was undertaken using a subset of the UK Biobank dataset.

Individuals were divided into males and females and each cohort was then ranked by LTL and grouped into deciles; shortest to longest. Next, for each LTL decile the retinal images of the individuals were presented to the Cardiac BioAge DL model and their Cardiac BioAge determined. Individuals in each LTL decile were then ranked by Cardiac BioAge, and the top and bottom quartile of each decile was determined. The mean of following variables derived from those individuals in the top quartile and the bottom quartile per LTL decile were compared: Systolic BP, HbA1C, PCE 10-year CVD risk scores.

Figure 9A:
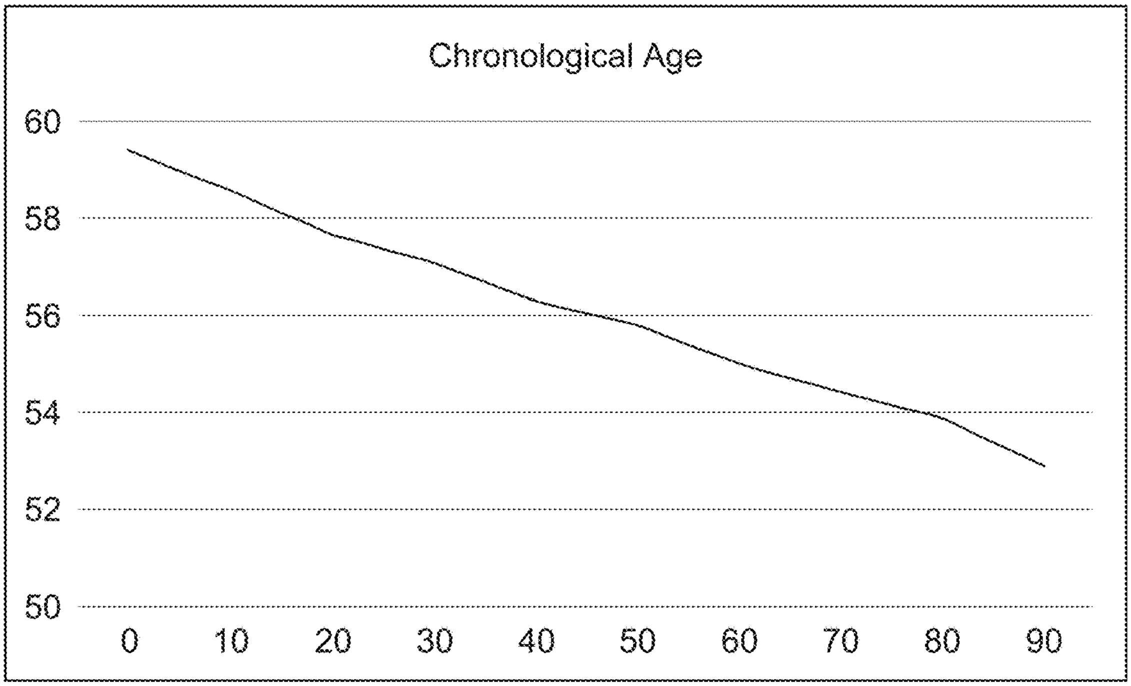
FIG. 9A shows the chronological age of males ranked by mean log LTL decile, in a study performed in accordance with aspects of the present technology.
Figure 9B:
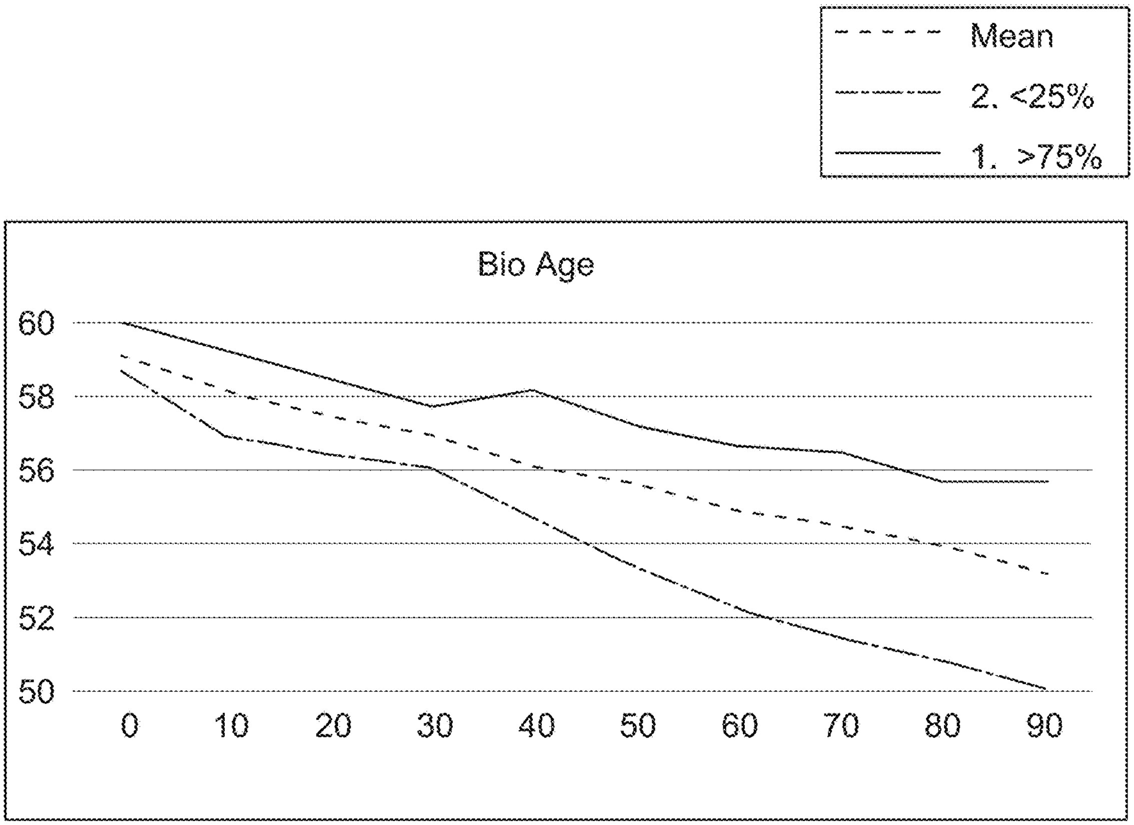
FIG. 9B shows the Cardiac BioAge issued by the DL model of males ranked by mean log LTL decile.
Figure 10A:
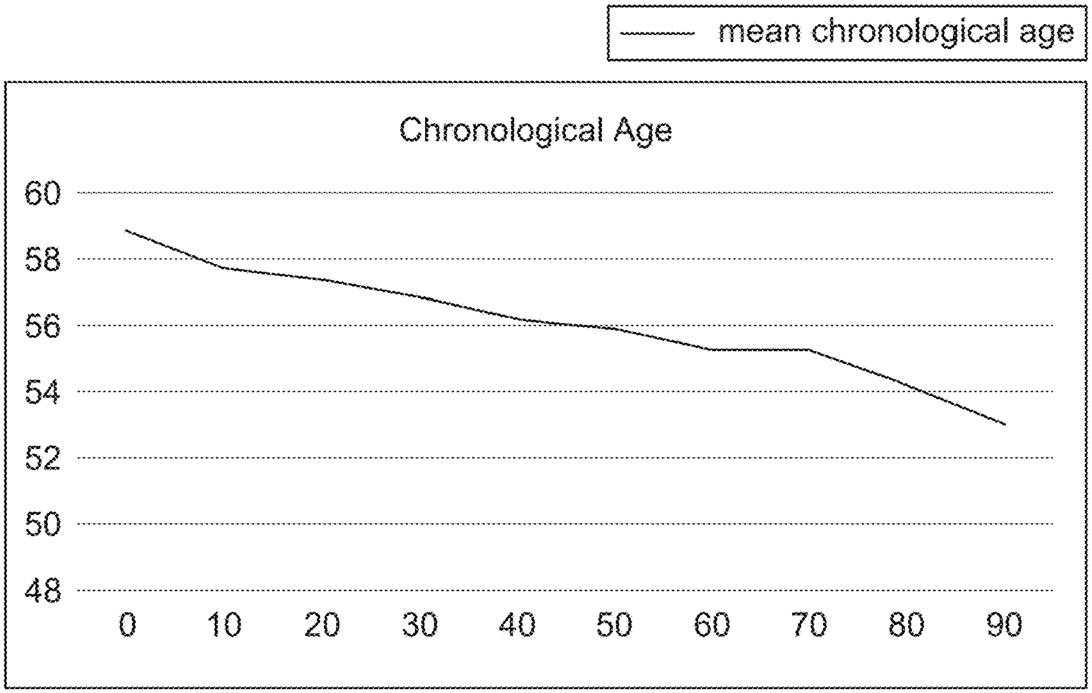
FIG. 10A shows the chronological age of females ranked by mean log LTL decile, in a study performed in accordance with aspects of the present technology.
Figure 10B:
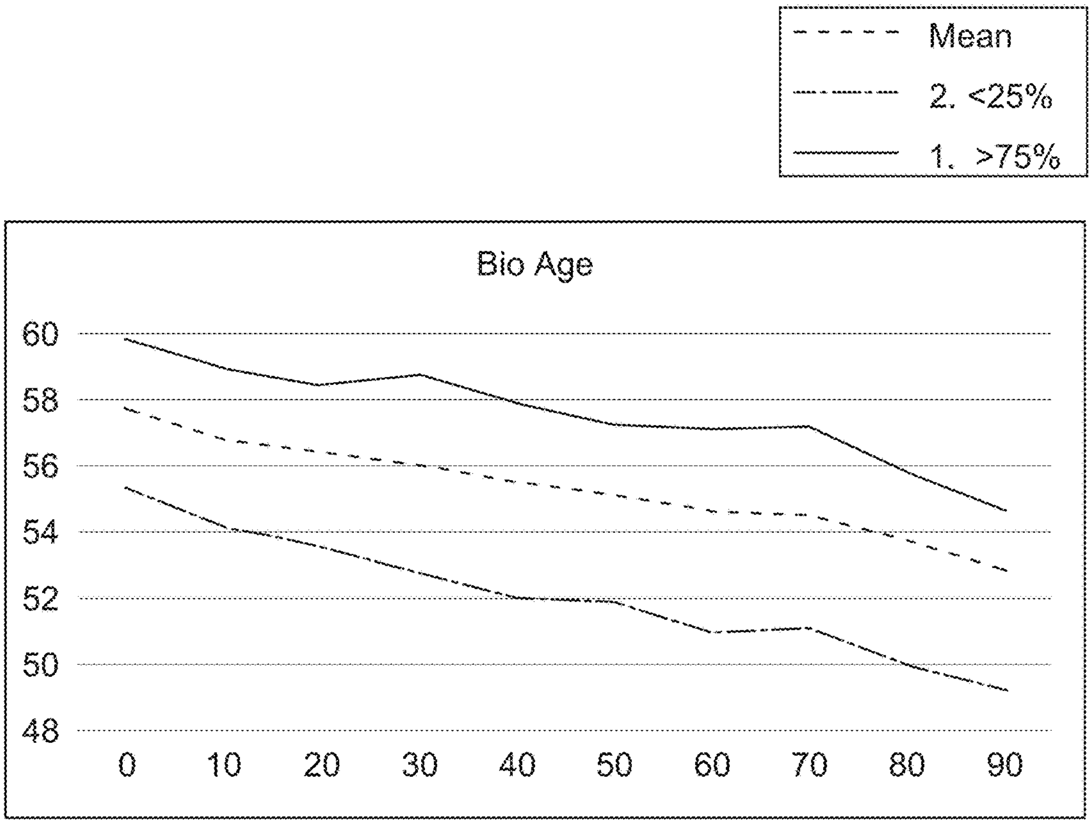
FIG. 10B shows the Cardiac BioAge issued by the DL model of females ranked by mean log LTL decile.
Figure 11A:
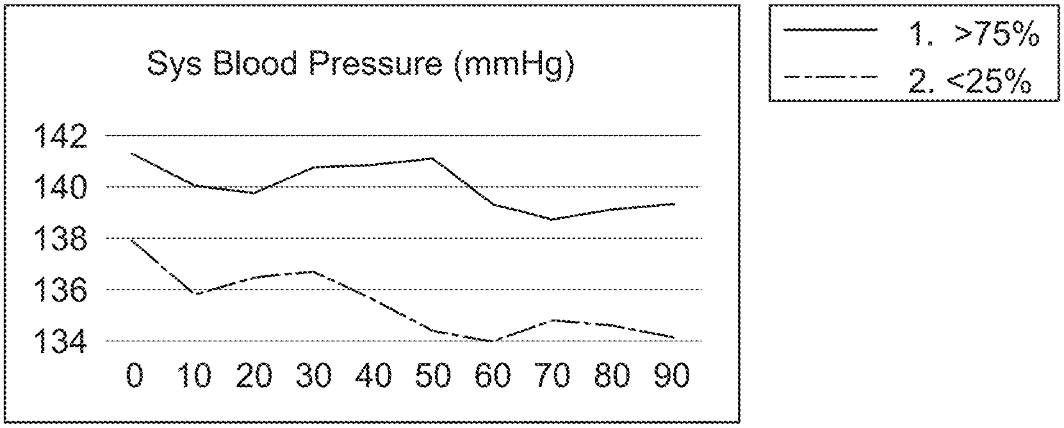
FIG. 11A to FIG. 11C show the Systolic Blood Pressure, HbA1C and 10-year PCE CVD risk score of those male individuals issued with a Cardiac BioAge score in the top quartile (Q1) and the bottom quartile (Q4) of their chronological peer group, categorised by mean log LTL decile.
Figure 11B:
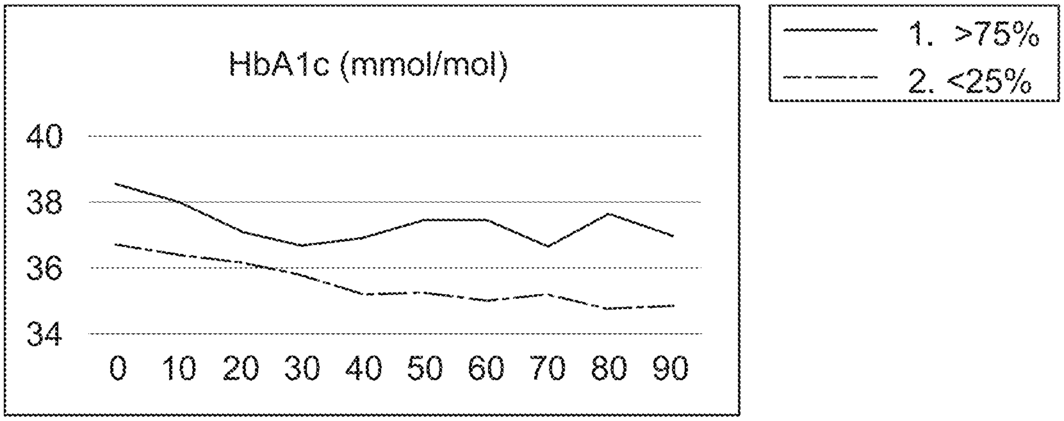
Figure 11C:
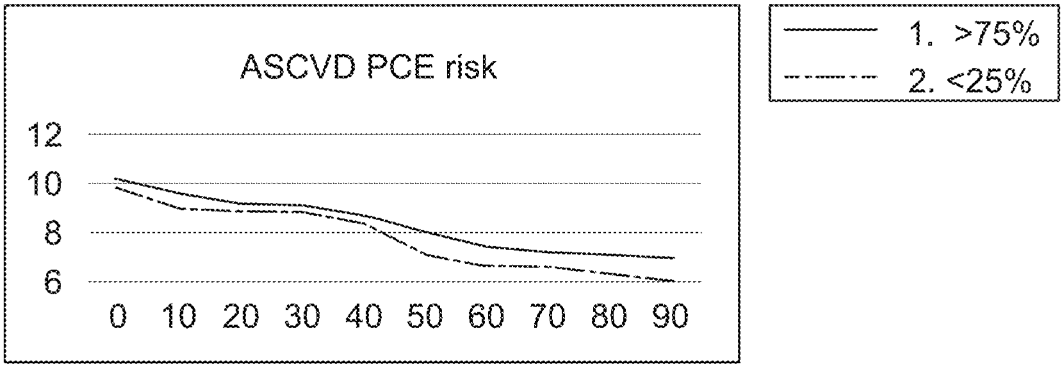
Figure 12A:
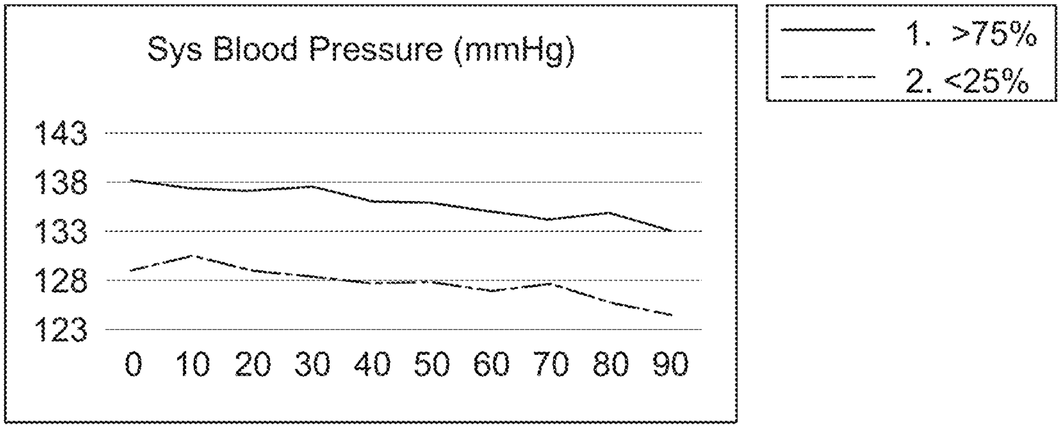
FIG. 12A to FIG. 12C show the Systolic Blood Pressure, HbA1C and 10-year PCE CVD risk score of those male individuals issued with a Cardiac BioAge score in the top quartile (Q1) and the bottom quartile (Q4) of their chronological peer group, categorised by mean log LTL decile.
Figure 12B:
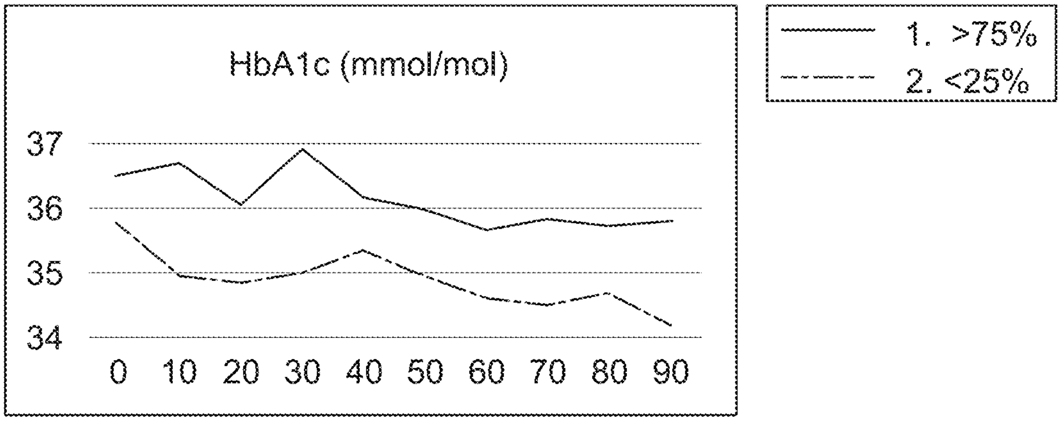
Figure 12C:
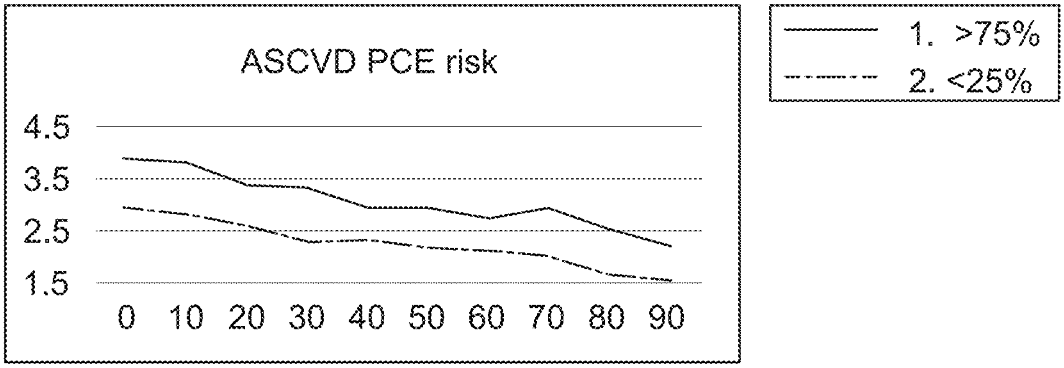

The chronological age and the Cardiac BioAge issued by the DL model of males ranked by mean log LTL decile are shown in FIGS. 9A and 9B respectively, and females in FIGS. 10A and 10B. The Systolic Blood pressure, HbA1C and 10-year PCE CVD risk score of those in individuals issued with a Cardiac BioAge score in the top quartile (Q1) and the bottom quartile (Q4) of their chronological peer group, categorised by mean log LTL decile is shown in FIGS. 11A to 11C (for males), FIGS. 12A to 12C (for females), and Table 14.

TABLE 14

Mean Biomarkers for male and female individuals in the top quartile of Cardiac BioAge (Q1) compared to the bottom Quartile (Q4) for their chronological peer group.

| | Males | | | Females | | |
|---|---|---|---|---|---|---|
| | Q1 Bioage Mean (Sd) | Q4 Bioage Mean (Sd) | P-value | Q1 Bioage Mean (Sd) | Q4 Bioage Mean (Sd) | P-value |
| Cardiac BioAge | 57 (2.0) | 54 (8.4) | P < 0.001 | 57 (1.4) | 52 (1.7) | P < 0.001 |
| SBP (mmHg) | 140 (0.8) | 135 (1.1) | P < 0.001 | 136 (1.5) | 127 (1.6) | P < 0.001 |
| HbA1c (mmol/mol) | 37 (0.5) | 35 (0.6) | P < 0.001 | 36 (0.4) | 34 (0.4) | P < 0.001 |
| 10-year CVD PCE risk score | 8% (1.0) | 7% (1.2) | P = 0.04 | 3% (0.5) | 2% (0.4) | P < 0.001 |

For both males and females, the mean systolic BP, mean HbA1C and the mean 10-year PCE CVD risk score, were all significantly higher in those individuals in the highest quartile of Cardiac BioAge compared to those in the lowest quartile of Cardiac BioAge (P<0.001)—see, Table 14. Furthermore, LTL were significantly shorter in males compared to older females, and in both males and females, increasing Chronological age and increasing Cardiac BioAge were both inversely correlated with LTL (see, FIGS. 9A and 9B and FIGS. 10A and 10B).

The inventors found that a worsening biomarker profile, increased chronological age and increased Cardiac BioAge were associated with LTL shortening. Additionally, they found the DL Cardiac BioAge model was able to accurately stratify patients into those at high risk of CVD and those at low risk of CVD disease as determined by relevant CVD biomarkers and the 10-year PCE derived CVD risk score. In line with traditional CVD models, both males and females who were issued with a Cardiac BioAge in the top quartile of their chronological peer group had a significantly higher mean SBP, HbA1C and 10-year PCE CVD score compared to those individuals in the bottom quartile (PCE etc).

It has been suggested that novel biomarkers such as LTL may also capture cardiac health, particularly by studies using Mendelian randomisation provide compelling evidence for a relationship between LTL shortening and an increased risk of both atherosclerotic cardiovascular events and an increased risk of hypertension. The rate of telomere shortening throughout life is suggested to be determined by both endogenous (genetic) and external (non-genetic) factors, and both appear to contribute to the association between LTL and CVD risk. At the time of application, the exact mechanism behind telomere length shortening and CVD remains to be elucidated, but it is thought that LTL may reflect both an individual's cumulative inflammatory exposure and oxidative stress and their genetically determined capacity to repair vascular damage. Irrespective of the mechanism by which LTL shorten, the results support a hypothesis that appropriately trained DL models can predict an individual's CVD risk as assessed by the traditional biomarkers, but may also be able to assess their risk by the novel biomarker LTL.

5. Cardiac BioAge Results Presentation

Figure 13:
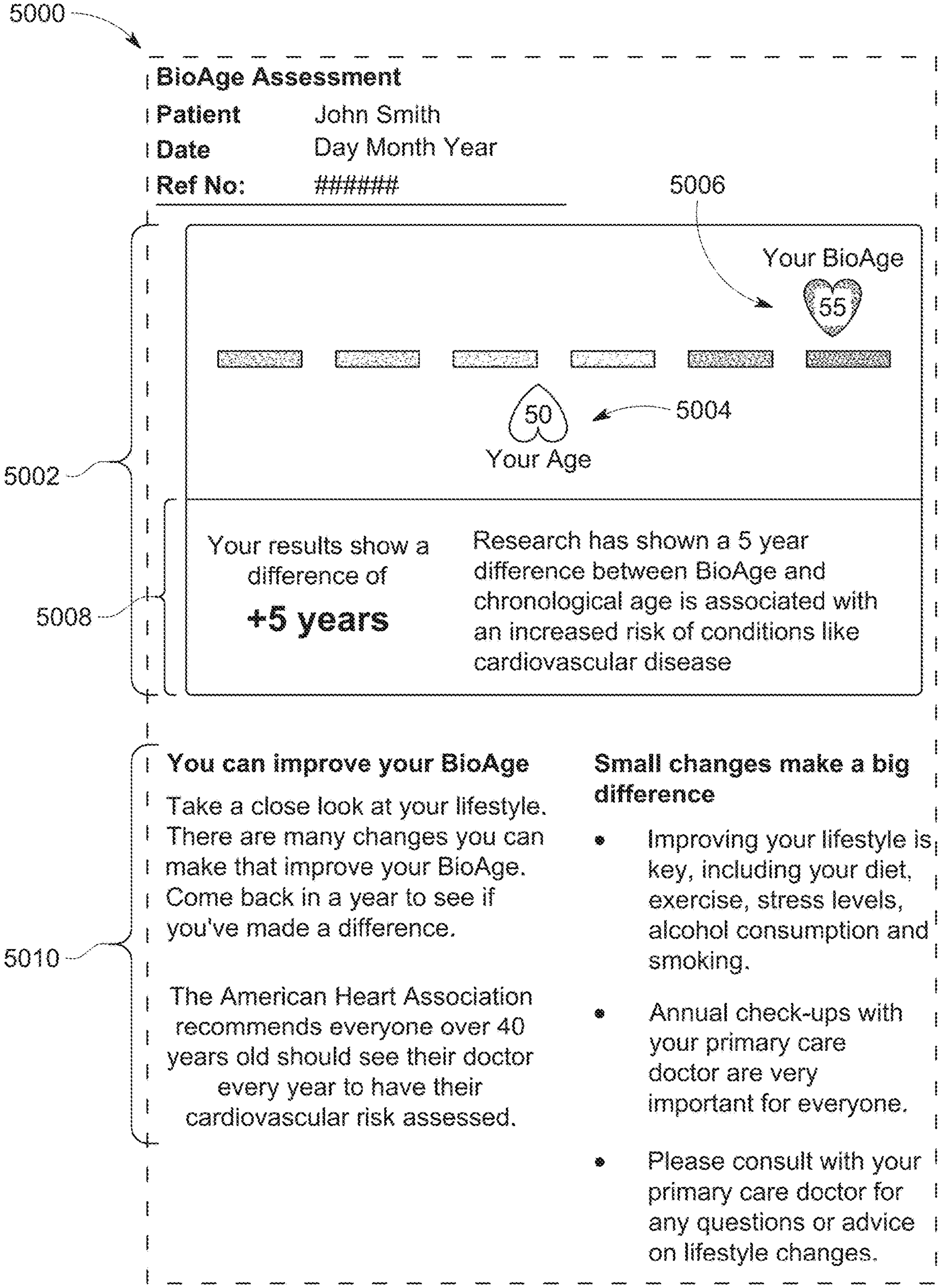
FIG. 13 illustrates an exemplary report of Cardiac BioAge produced in accordance with aspects of the present technology.

Referring to FIG. 13, the individual's Cardiac BioAge results may be presented in a report 5000, comprising an Cardiac BioAge infographic 5002 in which the individual's chronological age 5004 and Cardiac BioAge 5006 are indicated on a relative scale. In the illustrated example, the AgeGap is positive—i.e., their Cardiac BioAge is higher than their chronological age. A text explanation of this is provided in AgeGap section 5008.

An explanatory section 5010 summarises key recommendations for the individual to improve their Cardiac BioAge. In the illustrated example, a relatively high AgeGap has resulted in a relatively strong recommendation to make lifestyle changes with known links to health and wellbeing. These recommendations may be adjusted based on the individual's AgeGap—e.g., individuals with a negative or neutral AgeGap may be simply encouraged to continue monitoring their BioAge (such as on an annual basis), while individuals with a positive but not high AgeGap may be prompted to consider lifestyle changes.

The present technology offers the potential to significantly improve access to individualised recommendations for wellbeing—and in particular CVD risk prevention strategies—as the risk predictions they produce do not require either clinical or laboratory assessments to generate an individual's risk. As retinal photographs are routinely captured in Optometric practices it means the technology can be deployed without significant additional investment in primary care, a feature which makes these technologies particularly relevant to low-resource settings. Finally, AI-based prediction tools that assess risk at the individual level would inform treatment decisions based on the specific needs of an individual, thereby increasing the likelihood of positive health outcomes.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the field of endeavour in any country in the world.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The present disclosure may also be said broadly to consist in the parts, elements and features referred to or indicated in the specification of the application, individually or collectively, in any or all combinations of two or more of said parts, elements or features. Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the present disclosure and without diminishing its attendant advantages. It is therefore intended that such changes and modifications be included within the present disclosure as defined by the appended claims.

What is claimed is:

1. A method for determining at least one recommendation for management of wellbeing of a first individual, comprising:

determining an indication of relative cardiovascular aging of the first individual, based at least in part on a predicted risk of cardiovascular disease (CVD) of the individual determined by a deep learning model based on one or more fundus images; and determining the at least one recommendation for management of the individual's wellbeing based at least in part on the determined indication of relative cardiovascular aging of the first individual.

2. The method of claim 1, wherein determining an indication of relative cardiovascular aging of the first individual comprises:

determining a degree of similarity between a predicted risk of cardiovascular disease (CVD) of the first individual and the risk of CVD for a set of individuals belonging to a chronological age bracket to which the first individual also belongs, wherein the predicted risk of CVD is determined by a deep learning model based on one or more fundus images;

determining an average chronological age of individuals closest to the first individual in terms of predicted risk of CVD;

determining a mean expected chronological age for a person with the predicted risk of CVD of the first individual; and determining the indication of relative cardiovascular aging of the first individual based on the determined degree of similarity, the determined average chronological age, and the determined mean expected chronological age.

3. The method of claim 1, comprising determining a difference between an actual chronological age of the individual and the indication of relative cardiovascular aging of the first individual determined for the individual.

4. The method of claim 3, comprising comparing the age difference of the first individual with the age differences of a set of individuals belonging to a chronological age group to which the first individual belongs.

5. The method of claim 4, comprising determining a relative position of the first individual within the set of individuals based on age difference.

6. The method of claim 5, wherein determination of the at least one recommendation for management of the first individual's wellbeing is based at least in part on the relative position of the first individual within the set of individuals based on age difference.

7. The method of claim 1, comprising determining the relative contribution of one or more risk contributing factors to the indication of relative cardiovascular aging.

8. The method of claim 7, wherein the risk contributing factors include two or more of: blood pressure, glycated haemoglobin A1c (HbA1c), total cholesterol, and glycaemic control.

9. The method of claim 7, wherein the relative contribution of the one of more of the risk contributing factors is used to determine the at least one recommendation for management of the first individual's wellbeing.

10. The method of claim 1, wherein determining the indication of relative cardiovascular aging of the first individual comprises:

determining a degree of similarity between a predicted risk of cardiovascular disease (CVD) of the first individual and the risk of CVD for a set of individuals belonging to a chronological age bracket to which the first individual also belongs, wherein the predicted risk of CVD is determined by a deep learning model based on one or more fundus images;

determining an average chronological age of individuals closest to the first individual in terms of predicted risk of CVD;

determining a mean expected chronological age for a person with the predicted risk of CVD of the first individual; and determining the indication of relative cardiovascular aging of the first individual based on the determined degree of similarity, the determined average chronological age, and the determined mean expected chronological age.

11. The method of claim 10, wherein determining the indication of relative cardiovascular aging of the first individual ("Cardiac BioAge") comprises the calculation:

$$\text{Cardiac } BioAge_x = P(\text{risk}(x)|x \in X) * \underline{\text{age}(X)} + (1 - P(\text{risk}(x)|x \in X)) * \underline{\text{age}(Y|x \sim Y)}$$

where x refers to the first individual, and X is the set of individuals who are in the same age group as the first individual;

where P(risk(x)|x∈X) is the conditional probability that first individual x has CVD risk, risk(x), given that that the first individual belongs the set X of individuals who have similar age;

where $\underline{\text{age}(X)}$ is the mean age for set X; and where $\underline{\text{age}(Y|x\sim Y)}$ is the mean age of patient points who are close to the first individual x.

12. The method of claim 11, wherein the set of individuals comprises individuals of the same gender as the first individual.

13. The method of claim 11, wherein implementation of $\underline{\text{age}(Y|x\sim Y)}$ comprises the $$\text{components similarity magnitude} * \text{cosine similarity age} + (1 - \text{similarity magnitude}) * \text{risk extrapolated age.}$$

14. A system for determining at least one recommendation for management of wellbeing of a first individual, the system comprising one or more processors and one or more storage devices storing instructions that when executed by the one or more processors cause the one or more processors to perform operations comprising:

determining an indication of relative cardiovascular aging of the first individual, based at least in part on a predicted risk of cardiovascular disease (CVD) of the individual determined by a deep learning model based on one or more fundus images; and determining the at least one recommendation for management of the individual's wellbeing based at least in part on the indication of relative cardiovascular aging of the first individual determined.

15. A computer program product for determining a recommendation for management of wellbeing of a first individual, the computer program product comprising a non-transitory computer-readable storage medium containing computer program code for:

determining an indication of relative cardiovascular aging of the first individual, based at least in part on a predicted risk of cardiovascular disease (CVD) of the individual determined by a deep learning model based on one or more fundus images; and determining the at least one recommendation for management of the individual's wellbeing based at least in part on the indication of relative cardiovascular aging of the first individual determined.

* * * * *